United States Patent
Castano Galindo et al.

(10) Patent No.: US 12,285,157 B1
(45) Date of Patent: *Apr. 29, 2025

(54) ULTRA-SLIM ENDOSCOPY DEVICE SHAFT WITH PRECISE ORDINATE FOUR-WAY TIP CONTROL AND PRECISION STEERING WIRE ATTACHMENT

(71) Applicant: EvoEndo, Inc., Centennial, CO (US)

(72) Inventors: David Castano Galindo, Fort Lauderdale, FL (US); Blake Monjar, Pompano Beach, FL (US); Damian Tomlin, Coral Springs, FL (US); Paul Imaoka, Jacksonville, FL (US); Joel Friedlander, Englewood, CO (US)

(73) Assignee: EVOENDO, INC., Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/927,455

(22) Filed: Oct. 25, 2024

(51) Int. Cl.
*A61B 1/005* (2006.01)
*A61B 1/015* (2006.01)
*A61B 1/273* (2006.01)

(52) U.S. Cl.
CPC .......... *A61B 1/0057* (2013.01); *A61B 1/0052* (2013.01); *A61B 1/015* (2013.01); *A61B 1/2736* (2013.01)

(58) Field of Classification Search
CPC ..... A61B 1/0057; A61B 1/0052; A61B 1/015; A61B 1/2736; A61B 1/05; A61B 1/00066
See application file for complete search history.

(56) References Cited

U.S. PATENT DOCUMENTS

| | | | | |
|---|---|---|---|---|
| 4,996,974 A | * | 3/1991 | Ciarlei | A61B 1/0052 138/120 |
| 2010/0168717 A1 | * | 7/2010 | Grasse | B29C 48/10 604/524 |
| 2013/0038930 A1 | * | 2/2013 | Vent | G02B 23/2476 359/362 |
| 2015/0174363 A1 | * | 6/2015 | Sutermeister | A61M 25/005 604/95.04 |
| 2017/0325660 A1 | * | 11/2017 | Wang | A61B 1/0052 |
| 2020/0008687 A1 | * | 1/2020 | Friedlander | A61B 3/16 |
| 2022/0175226 A1 | * | 6/2022 | Sørensen | A61B 1/07 |
| 2024/0216093 A1 | * | 7/2024 | Furtado | A61B 34/37 |

* cited by examiner

*Primary Examiner* — Anh Tuan T Nguyen
*Assistant Examiner* — Rynae E Boler
(74) *Attorney, Agent, or Firm* — Farber LLC

(57) ABSTRACT

Systems and methods are disclosed for an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough. The shaft may include an outer jacket defining an outer surface of the shaft, and an inner channel defining a working channel extending longitudinally through the shaft. The shaft defines an open space between the outer jacket and the inner channel, with an electrical wire for an illumination and/or a camera device extending longitudinally within the open space. The open space may improve the flexibility of the shaft along its entire length thereby improving patient comfort, and may also enable the steering wires to be positioned for improved up/down and left/right movement relative to the steering inputs provided by the user.

29 Claims, 20 Drawing Sheets

ULTRA-SLIM ENDOSCOPY DEVICE SHAFT WITH PRECISE ORDINATE FOUR-WAY TIP CONTROL AND PRECISION STEERING WIRE ATTACHMENT

BACKGROUND

Eosinophilic esophagitis (EoE) is an increasingly common chronic inflammatory disease that affects children and adults. Because of its potential to progress to esophageal stricture and the fact that symptoms do not always correlate with degree of eosinophilia, much attention has been paid to repeated assessment of the esophageal mucosa to ensure mucosal healing following treatment. In contrast, the risks, cost and time commitment associated with traditional sedated esophagogastroduodenoscopy (EGD) can be significant and have raised concerns for providers and patients alike. To address these questions, alternative methods are needed to measure esophageal inflammation. In addition to esophagoscopy with biopsies, other technologies such as the Cytosponge, esophageal string test and confocal tethered endomicroscopy have emerged as potential alternatives for assessing mucosal inflammation.

Recent work has led to the development of trans-nasal endoscopy/esophagoscopy (TNE) to assess the esophageal mucosa in adults. In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. However, the endoscopes used in the adult procedures are not appropriate for use in pediatric setting and, in fact, may be too large for many adults.

During a trans-nasal endoscopic procedure, patients may experience physical discomfort due to the endoscope being inserted into the nose, through the sinus cavities and down into the esophagus. This physical discomfort, or even the fear of being uncomfortable, can make trans-nasal endoscopy procedures mentally and emotionally distressing for a patient, too. Because it is desirable to make the procedure mentally and physically easier on the patient, it would be advantageous to optimize the endoscope being used for the procedure.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The trans-nasal endoscope described hereinbelow, according to various embodiments, addresses various challenges. For example, the trans-nasal endoscope described hereinbelow, according to various embodiments, provides a device and associated methodology that can be used to adapt TNE to assess the esophageal mucosa, gastric, and duodenal, tracheal, and bronchial mucosa in children and small adults in both a sedated and unsedated manner with a full array of steering and visualization capabilities. The trans-nasal endoscope described hereinbelow, according to various embodiments, provides a scope that minimizes the outer diameter thereof, e.g., to reduce the discomfort to patients, while maximizing the diameter of the working channel, e.g., to provide the largest possible channel through which tools may be introduced, while simultaneously providing enhanced, e.g., four-way, steering capabilities as well as visualization functionality, as will be described more fully below. In various embodiments, the outer diameter of the endoscope shaft may be 5.0 mm or less, preferably may be less than about 4.5 mm, and preferably is about 3.5 mm. In addition, in various embodiments, the diameter of the working channel may have a range of about 1.5 mm to 2.8 mm, and preferably is about 2.0 mm.

It is noted that, according to various embodiments, the endoscope described herein may be particularly well-suited for unsedated surgical procedures. Sedation is well-known, in certain circumstances, to present various risks to patients, but is often employed during surgical procedures to prevent a patient from experiencing discomfort or anxiety. By providing an endoscope having, e.g., a minimized outer diameter, a more flexible and more steerable distal regions (as will be explained in further detail below) among other advantages described below, patient discomfort and anxiety may be reduced, thereby enabling surgical procedures to be performed in an unsedated, and thus more safe, manner.

It should be recognized that, while the scope set forth herein is described hereinbelow for use in a trans-nasal endoscopy procedure, it may also be employed in a variety of other medical or surgical applications. For example, the scope set forth herein may be employed for use as a nasal endoscope, a trans-nasal esophagoscope, a trans-nasal gastroscope, a trans-nasal duodenoscope, a trans-nasal enteroscope, a triple endoscope, a bronchoscope, a laryngoscope, a trans-nasal gastroscope, an aerodigestive scope, and/or an endoscopic device used to visualize any body cavity into which it would fit, e.g., for examination of a stricture or the like. It should also be recognized that the endoscope described herein may be employed in fetal surgical procedures, and/or in surgical procedures that employ natural orifices, e.g., NOTES or natural orifice transluminal endoscopic procedures, such as trans-orally, trans-anally, trans-vaginally or any other natural orifice. The discussion herein of a pediatric trans-nasal endoscopy procedure is merely exemplary.

In accordance with various embodiments thereof, systems and methods are provided for use in a surgical procedure. In an embodiment, there is provided an endoscope for use in a surgical procedure, e.g., a pediatric trans-nasal endoscopy procedure, that includes a handle for gripping by a user, and a shaft extending from the handle. The shaft may have a working channel extending longitudinally therethrough. The shaft may also have a proximal region at or adjacent to the handle and a distal region configured to be inserted into a patient. In an embodiment, the exterior of the shaft may be protected by a laminate layer. The laminate layer of the proximal region of the shaft may have a first flexibility and the laminate layer of the distal region of the shaft may have a second flexibility that is more flexible than the first flexibility. In this way, the distal region of the shaft may be more flexible than the proximal region of the shaft for improved steering capabilities.

The shaft may have a shaft wall having an inner diameter defined by the working channel and an outer diameter that is adjacent to and enclosed by the laminate layer. The shaft wall may be comprised of braided filaments so as to minimize the outer diameter of the shaft wall while maximizing the diameter of the working channel, and thereby help enable the shaft to be configured for use in pediatric trans-nasal endoscopy procedures.

In further embodiments, the shaft may have a central region located longitudinally between the proximal region and the distal region. In this embodiment, the laminate layer of the central region may have a flexibility that may be more flexible than the first flexibility of the proximal region of the shaft, and that may be less flexible than the second flexibility of the distal region. In embodiments, the laminate layer of the distal region may be Pebax® 35D, the laminate layer of the central region may be Pebax® 55D, and the laminate layer of the proximal region may be Polyimide.

In further embodiments, the endoscope may also include at least one steering wire extending longitudinally within the shaft and parallel to the working channel. The steering wire may have a steering mechanism on the handle and may be actuatable by user to steer at least the distal region of the shaft. Still further, the endoscope may also include an illumination source and an imaging device, e.g., camera, located at the distal end of the shaft. The illumination source and the camera may be connected to and controlled by an electronic control module on the handle. An electrical cable may extend longitudinally within the shaft and parallel to the working channel. The endoscope may also include a control mechanism in the handle actuatable by a user to selectively control the flow of at least one of air, suction or water through the working channel. In embodiments, the working channel may include an instrument port through which a surgical instrument can be introduced into and through the working channel. In addition, the working channel may include a bifurcation region that splits the working channel into a first channel and a second channel. In this case, the first channel may have an instrument port through which a surgical instrument can be introduced into the working channel, and the second channel may be configured to convey at least one of air, suction or water into the working channel via a control mechanism in the handle actuatable by a user.

In still further embodiments, there is provided an endoscope for use in a surgical procedure, e.g., such as a pediatric trans-nasal endoscopy procedure, that includes a handle for gripping by a user and a shaft extending from the handle. The shaft may have a distal region configured to be inserted into a patient, and a shaft wall with an inner diameter and an outer diameter. The inner diameter may be defined by a working channel extending longitudinally through the shaft. The shaft may also include at least one wire extending longitudinally through the shaft wall between the inner diameter and the outer diameter. The shaft wall may be comprised of braided filaments that are woven over and under the at least one wire so as to maintain the at least one wire between the inner and outer diameters of the shaft wall.

In various embodiment, the at least one wire may be a steering wire actuatable by a user via a steering mechanism on the handle to steer at least the distal region of the shaft. Advantageously, the endoscope may have four steering wires, and the braided filaments of the shaft wall may be woven over and under the four steering wires so as to maintain the four steering wires between the inner and outer diameters of the shaft wall, while providing, e.g., four-way steering capabilities.

In various embodiments, the endoscope may also include an illumination source and an imaging device located at the distal end of the shaft. The illumination source and the imaging device may be connected to and controlled by an electronic control module on the handle. In this case, the at least one wire may be an electrical cable that connects the electronic control module to the illumination source and imaging device. In embodiments, the braided filaments of the shaft wall may be woven over and under the four steering wires and the electrical cable so as to maintain the four steering wires and the electrical cable between the inner and outer diameters of the shaft wall.

In some embodiments, the shaft may have a proximal region adjacent to the handle. The exterior of the shaft may be protected by a laminate layer. The laminate layer of the proximal region of the shaft may have a first flexibility and the laminate layer of the distal region of the shaft may have a second flexibility that is more flexible than the first flexibility. In this way, the distal region of the braided shaft may be more flexible than the proximal region of the shaft.

In various embodiments, the endoscope may also include a control mechanism in the handle. The control mechanism may be actuatable by a user to selectively control the flow of at least one of air, suction or water through the working channel. In addition, the working channel may include an instrument port through which a surgical instrument can be introduced into the working channel. Advantageously, the working channel may include a bifurcation region that splits the working channel into a first channel and a second channel. The first channel may have an instrument port through which a surgical instrument can be introduced into the working channel, and the second channel may be configured to convey at least one of air, suction or water into the working channel via a control mechanism in the handle that is actuatable by a user.

In still further embodiments, there is provided an endoscope for use in a surgical procedure, e.g., a pediatric trans-nasal endoscopy procedure. The endoscope may include a handle for gripping by a user, the handle having a steering control mechanism. The endoscope may also include a shaft extending from the handle. The shaft may have a working channel extending longitudinally therethrough. In addition, the shaft may have a distal region configured to be inserted into a patient. The endoscope may also include at least two steering wires extending longitudinally through the shaft and parallel to the working channel. The at least two steering wires may extend from the distal region of the shaft to the steering control mechanism of the handle. Still further, the steering control mechanism may include first and second actuators located on opposite sides of the handle. The first and second actuators may be actuatable by a user to allow ambidextrous steering of at least the distal region of the shaft.

In embodiments, the first and second actuators may control steering of the distal region of the shaft in the left and right directions. The first and second actuators may include first and second rollers, the first and second rollers each having one of the at least two steering wires attached thereto. The steering mechanism may also include a third actuator configured to control steering of the distal region of the shaft in the up and down directions. In this case, the endoscope may include a third steering wire to which the third actuator may be attached. The third actuator may include a thumb knob extending from the proximal end of the handle. The endoscope may also include a steering collar located at the distal region of the shaft. The steering wires may be connected to the steering collar at circumferentially spaced apart locations. The steering wires may be pulled by the actuators so as to selectively move such locations of the steering collar to steer the distal region of the shaft.

In various embodiments, the endoscope also includes a control mechanism in the handle actuatable by a user to selectively control the flow of at least one of air, suction or water through the working channel. Furthermore, the endoscope may also include an illumination source and an imaging device located at a distal end of the shaft. The illumination source and the imaging device may be connected to and controlled by an electronic control module on the handle via an electrical cable. The electrical cable may extend longitudinally within the shaft and parallel to the working channel. In addition, the working channel may include an instrument port through which a surgical instrument can be introduced into the working channel.

In still further embodiments, there is provided an endoscope for use in a surgical procedure that comprises a handle for gripping by a user and a shaft extending from the handle and having a working channel extending longitudinally therethrough, the shaft configured to be longitudinally inserted into a nasal opening of a patient until the shaft reaches a fully-inserted position within the patient. When the shaft is in the fully-inserted position, the shaft has an extracorporeal zone configured to reside proximal relative to the patient's nasal opening and having a first flexibility. When the shaft is in the fully-inserted position, the shaft may also have a patient comfort zone extending distally from the extracorporeal zone and that is configured to reside from the patient's nose through the patient's pharynx and to a top of the patient's esophagus, the patient comfort zone having a second flexibility that is more flexible than the first flexibility. When the shaft is in the fully-inserted position, the shaft may also have a distal functional endoscopic zone extending distally from the patient comfort zone and may be configured to reside from the top of the patient's esophagus to a distalmost tip of the shaft.

In various embodiments, the distal functional endoscopic zone may also include an esophageal working zone extending distally from the patient comfort zone and configured to reside from the top of the patient's esophagus to a top of the patient's stomach, the esophageal working zone having a third flexibility that is less flexible than the second flexibility. In still other embodiments, the distal functional endoscopic zone may further comprise a distalmost zone at the distalmost end of the shaft, the distalmost zone including a distal tip that includes an electronic component, the distalmost zone also including a distal flex zone having a fourth flexibility that is more flexible than the esophageal working zone.

In various embodiments, the distal functional endoscopic zone further comprises a stomach working zone positioned longitudinally between the esophageal working zone and the distalmost zone, the stomach working zone being configured to reside within the patient's stomach.

In various embodiments, the exterior of the shaft may be protected by a laminate layer, wherein the different flexibilities are due to at least in part to the extracorporeal zone and the patient comfort zone having different laminate layers. For example, the laminate layer of at least one zone is Pebax® 55D, the laminate layer of at least a second zone is Pebax® 72D.

In various embodiments, the shaft may have a shaft wall having an inner diameter defined by the working channel and an outer diameter that is adjacent to and enclosed by the laminate layer, the shaft wall being comprised of braided filaments, wherein the different flexibilities are due at least in part to the extracorporeal zone and the patient comfort zone having braided filaments having a different number of braid per linear inch.

The shaft, according to various embodiments, may have a length up to about 220 cm. In a specific embodiments, the shaft may have a length of about 85 cm. In such an embodiment, the shaft may have a length of about 85 cm, and the extracorporeal zone may have a length of about 25 cm, the patient comfort zone may have a length of about 30 cm, the esophageal working zone may have a length of about 23 cm, the distal flex zone may have a length of about 6 cm, and the distal tip may have a length of about 1 cm.

In still other embodiments, the shaft may have a length of about 110 cm. In such an embodiment, the shaft may have a length of about 110 cm, and the extracorporeal zone may have a length of about 25 cm, the patient comfort zone may have a length of about 30 cm, the esophageal working zone may have a length of about 23 cm, the stomach working zone may have a length of about 25 cm, the distal flex zone may have a length of about 6 cm, and the distal tip may have a length of about 1 cm.

According to various embodiments, the endoscope may also include at least one steering wire extending longitudinally within the shaft and parallel to the working channel, the steering wire having a steering mechanism on the handle and being actuatable by user to steer at least the distal region of the shaft. Still further, the at least one steering wire may be four steering wires, the braided filaments of the shaft wall being woven over and under the four steering wires so as to maintain the four steering wires between the inner and outer diameters of the shaft wall.

In addition, the electronic component may include at least one of an illumination source and an imaging device, the illumination source and the imaging device being connected via an electrical cable to an electronic control module on the handle, the electrical cable extending longitudinally within the shaft and parallel to the working channel. The endoscope may also include a control mechanism in the handle actuatable by a user to selectively control the flow of at least one of air, suction or water through the working channel. Still further, the working channel may include an instrument port through which a surgical instrument can be introduced through the working channel.

In still further embodiments, there is provided an endoscope for use in a surgical procedure that comprises a handle for gripping by a user and a shaft extending from the handle and having a working channel extending longitudinally therethrough, the shaft configured to be longitudinally inserted into a nasal opening of a patient until the shaft reaches a fully-inserted position within the patient. When the shaft is in the fully-inserted position, the shaft may have an extracorporeal zone configured to reside proximal relative to the patient's nasal opening and having a first flexibility. When the shaft is in the fully-inserted position, the shaft may also have a patient comfort zone extending distally from the extracorporeal zone and configured to reside from the patient's nose through the patient's pharynx and to a top of the patient's esophagus, the patient comfort zone having a second flexibility that is more flexible than the first flexibility. When the shaft is in the fully-inserted position, the shaft may further have an esophageal working zone extending distally from the patient comfort zone and configured to reside from the top of the patient's esophagus to a top of the patient's stomach, the esophageal working zone having a third flexibility that is less flexible than the second flexibility. When the shaft is in the fully-inserted position, the shaft may still further have a distal flex zone having a fourth flexibility that is more flexible than the esophageal working zone and a distal tip that includes an electronic component.

In various embodiments, the exterior of the shaft may be protected by a laminate layer, wherein the shaft has a shaft wall having an inner diameter defined by the working channel and an outer diameter that is adjacent to and enclosed by the laminate layer, the shaft wall being comprised of braided filaments, and wherein the different flexibilities are at least partially due to at least one of the zones having a different laminate layer or a different number of braid per line inch.

In various embodiments, the shaft may have a length of about 85 cm, and the extracorporeal zone may have a length of about 25 cm, the patient comfort zone may have a length of about 30 cm, the esophageal working zone may have a length of about 23 cm, the distal flex zone may have a length of about 6 cm, and the distal tip may have a length of about 1 cm.

The endoscope may laos include, in various embodiments, at least one steering wire extending longitudinally within the shaft and parallel to the working channel, the steering wire having a steering mechanism on the handle and being actuatable by user to steer at least the distal region of the shaft. The at least one steering wire may be four steering wires, the braided filaments of the shaft wall being woven over and under the four steering wires so as to maintain the four steering wires between the inner and outer diameters of the shaft wall.

Still further, the electronic component may include at least one of an illumination source and an imaging device, the illumination source and the imaging device being connected via an electrical cable to an electronic control module on the handle, the electrical cable extending longitudinally within the shaft and parallel to the working channel. The endoscope may also include a control mechanism in the handle actuatable by a user to selectively control the flow of at least one of air, suction or water through the working channel. Still further, the working channel may include an instrument port through which a surgical instrument can be introduced through the working channel.

In still further embodiments, there is provided an endoscope for use in a surgical procedure that comprises a handle for gripping by a user and a shaft extending from the handle. The shaft may have a working channel extending longitudinally therethrough, the shaft may be configured to be longitudinally inserted into a nasal opening of a patient until the shaft reaches a fully-inserted position within the patient. When the shaft is in the fully-inserted position, the shaft may have i) an extracorporeal zone configured to reside proximal relative to the patient's nasal opening and having a first flexibility; ii) a patient comfort zone extending distally from the extracorporeal zone and configured to reside from the patient's nose through the patient's pharynx and to a top of the patient's esophagus, the patient comfort zone having a second flexibility that is more flexible than the first flexibility; iii) an esophageal working zone extending distally from the patient comfort zone and configured to reside from the top of the patient's esophagus to a top of the patient's stomach, the esophageal working zone having a third flexibility that is less flexible than the second flexibility; iv) a stomach working zone extending distally from the esophageal working zone, the stomach working zone being configured to reside within the patient's stomach; v) a distal flex zone extending distally from the stomach working zone and having a fourth flexibility that is more flexible than the esophageal working zone; and vi) a distal tip that includes an electronic component.

In various such embodiments, the exterior of the shaft may be protected by a laminate layer, and the shaft may have a shaft wall having an inner diameter defined by the working channel and an outer diameter that is adjacent to and enclosed by the laminate layer. The shaft wall may be comprised of braided filaments, and the different flexibilities may be at least partially due to at least one of the zones having a different laminate layer or a different number of braid per line inch.

In various embodiments, the shaft may have a length of about 110 cm, and the extracorporeal zone may have a length of about 25 cm, the patient comfort zone may have a length of about 30 cm, the esophageal working zone may have a length of about 23 cm, the stomach working zone may have a length of about 25 cm, the distal flex zone may have a length of about 6 cm, and the distal tip may have a length of about 1 cm.

Still further, the endoscope may include four steering wire extending longitudinally within the shaft and parallel to the working channel, the steering wires having a steering mechanism on the handle and being actuatable by user to steer at least the distal region of the shaft, the braided filaments of the shaft wall being woven over and under the four steering wires so as to maintain the four steering wires between the inner and outer diameters of the shaft wall.

Still further, the electronic component may include at least one of an illumination source and an imaging device. The illumination source and the imaging device may be connected via an electrical cable to an electronic control module on the handle, the electrical cable extending longitudinally within the shaft and parallel to the working channel.

Additionally or alternatively, the endoscope may include a control mechanism in the handle actuatable by a user to selectively control the flow of at least one of air, suction or water through the working channel.

In still other embodiments, there is provided an endoscope for use in a surgical procedure, comprising a handle for gripping by a user and a shaft extending from the handle and configured to be longitudinally inserted into a patient. The shaft may include an outer jacket defining an outer surface of the shaft, and an inner channel defining a working channel extending longitudinally through the shaft. The shaft may define an open space between the outer jacket and the inner channel, with an electrical wire extending longitudinally within the open space.

In embodiments, the outer jacket may include braided filaments and/or an outer protective layer. In addition, the outer jacket may define a plurality of longitudinally-extending lumen., and may include a plurality of longitudinally-extending steering wires, each one of the plurality of longitudinally-extending steering wires extending through a respective one of the plurality of longitudinally-extending lumen. Each one of the plurality of longitudinally-extending lumen may be defined by a respective one of a plurality of tubular sheaths, the plurality of tubular sheaths being either or both of more lubricious and/or more durable than the material from which the outer jacket is formed, such that the steering wires may move more easily therewithin and/or such that the movement of the steering wires through the tubular sheaths does not damage the material of the outer jacket. The endoscope may also include at least one of an illumination source and an imaging device located at the distal end of the shaft, the illumination source and the imaging device being connected via the electrical wire to an electronic control module in the handle. The endoscope may also include a control mechanism in the handle actuatable by a user to selectively control the flow of at least one of air, suction or water through the working channel.

In still other embodiments, there is provided an endoscope for use in a surgical procedure, comprising a handle for gripping by a user, and a shaft extending from the handle and configured to be longitudinally inserted into a patient. The shaft may include an outer jacket, the outer jacket having an outer surface that defines an outer surface of the shaft, the outer jacket also having an inner surface. The shaft may also include an inner channel, the inner channel having an outer surface, the inner channel also having an inner surface defining a working channel extending longitudinally through the shaft. The shaft may define an open space between the inner surface of the outer jacket and the outer surface of the inner channel, whereby the open space between the inner surface of the outer jacket and the outer surface of the inner channel contributes to increasing the flexibility of the shaft along its entire length.

In embodiments, the endoscope also includes an electrical wire extending longitudinally within the open space. The outer jacket may include braided filaments and/or an outer protective layer. The outer jacket may define a plurality of longitudinally-extending lumen, and a plurality of longitudinally-extending steering wires, wherein each one of the plurality of longitudinally-extending steering wires extend through a respective one of the plurality of longitudinally-extending lumen. Each one of the plurality of longitudinally-extending lumen may be defined by a respective one of a plurality of tubular sheaths. The plurality of tubular sheaths may be more lubricious than the material from which the outer jacket is formed, such that the steering wires may move more easily therewithin, and/or the plurality of tubular sheaths may be formed from a material that is more durable than the material from which the outer jacket is formed, such that the movement of the steering wires through the tubular sheaths does not damage the material of the outer jacket. The endoscope may also include at least one of an illumination source and an imaging device located at the distal end of the shaft, the illumination source and the imaging device being connected via the electrical wire to an electronic control module in the handle.

In still other embodiments, there is provided an endoscope for use in a surgical procedure, comprising a handle for gripping by a user, the handle including roller knobs, and a shaft extending from the handle and configured to be longitudinally inserted into a patient. The shaft may also include an outer jacket defining an outer surface of the shaft, the outer jacket defining a plurality of longitudinally-extending lumen. The shaft may also include a plurality of longitudinally-extending steering wires, each one of the plurality of longitudinally-extending steering wires extending through a respective one of the plurality of longitudinally-extending lumen, wherein the plurality of longitudinally-extending steering wires arranged at 0, 90, 180 and 270 degrees around the circumference of the shaft as measured from the topmost region of the shaft. The plurality of longitudinally-extending steering wires may be connected to the respective roller knobs on the handle such that movement by a user of the roller knobs causes corresponding movement of the shaft in 0, 90, 180 and 270 degree directions, improving predictability and alignment of the user's movement of the roller knobs with the steering of the shaft.

In embodiments, the outer jacket may also have an inner surface. The shaft may also include an inner sheath, the inner sheath having an outer surface, the inner sheath also having an inner surface defining a working channel extending longitudinally through the shaft. The shaft may include an open space between the inner surface of the outer jacket and the outer surface of the inner channel. In embodiments, an electrical wire may extend longitudinally within the open space.

Furthermore, the outer jacket may include braided filaments. Also, the outer jacket may include an outer protective layer. Each one of the plurality of longitudinally-extending lumen may be defined by a respective one of a plurality of tubular sheaths. The plurality of tubular sheaths may be more lubricious than the material from which the outer jacket is formed, such that the steering wires may move more easily therewithin, and/or the plurality of tubular sheaths may be more durable than the material from which the outer jacket is formed, such that the movement of the steering wires does not damage the material of the outer jacket.

It should be noted, of course, that to the extent that images, e.g., image signals, image data, etc., are described herein, it will be understood that such also refers to video, e.g., video signals, video data, etc., and that the description of the image signals is intended to include single images, still images, video images, etc. without limitation.

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures, components, circuits, and networks have not been described in detail so as not to unnecessarily obscure aspects of the embodiments.

Figure 1:
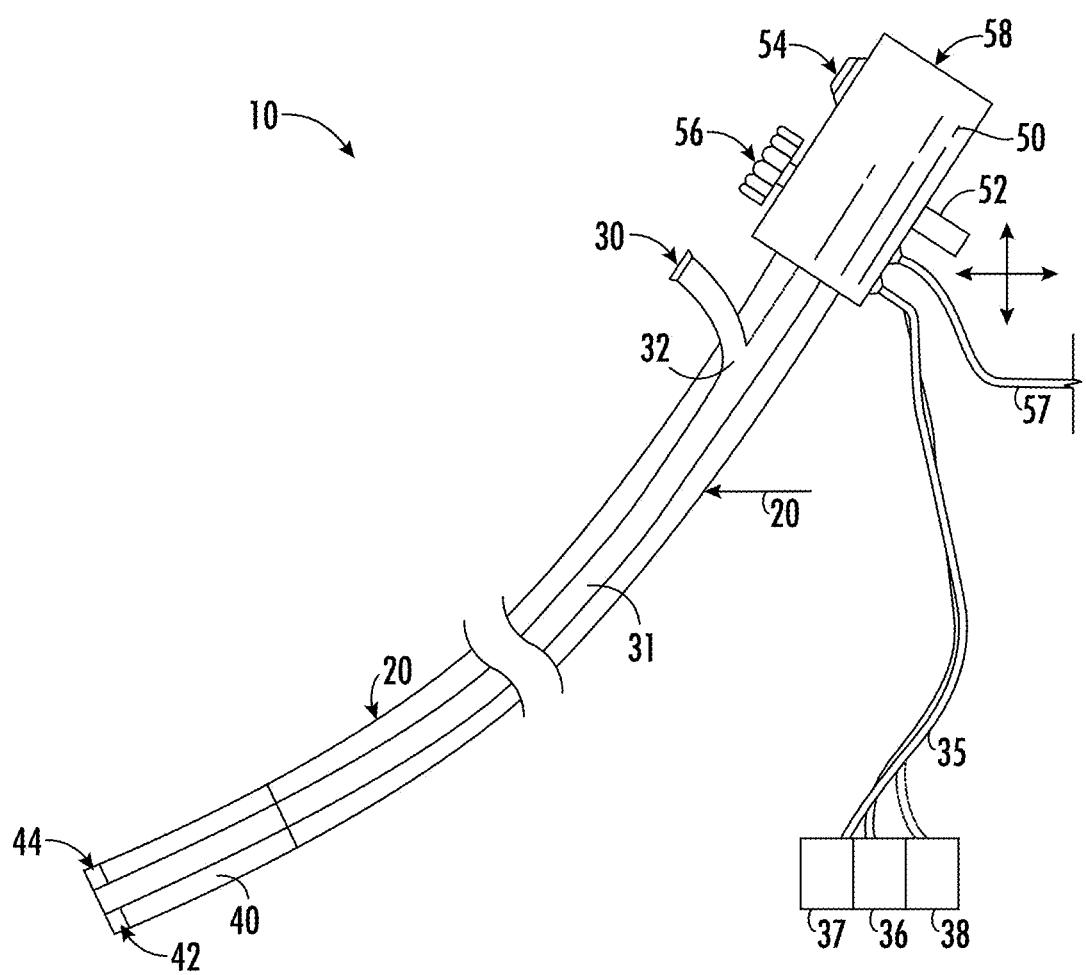
FIG. 1 shows a schematic representation of a trans-nasal endoscope that includes a flexible endoscope shaft, in accordance with various embodiments.

FIG. 1 is a schematic diagram of a trans-nasal endoscope 10, according to one example embodiment, illustrating some of the various features thereof. As mentioned previously, while the example embodiments set forth hereinbelow are described as an endoscope that is suitable for trans-nasal insertion into a patient, and is particularly well-suited for trans-nasal insertion into a child or small adult, it is understood that this is merely one example embodiment, and that the description hereinbelow of a trans-nasal endoscope does not preclude the use of the device in other types of procedures and for other types of patients. It should be noted that FIG. 1 is merely schematic, and thus the shape and position of the various features illustrated therein are merely exemplary. Additional figures, illustrating specific embodiments of the various features and functionality, will be provided in further detail below.

In the embodiment shown schematically in FIG. 1, the trans-nasal endoscope 10 includes a flexible endoscope shaft 20. The flexible endoscope shaft 20 has a working channel 31. The working channel 31 extends longitudinally from a distal end 40 of the endoscope shaft 20 proximally towards a handle 50 located at or near the proximal end of the trans-nasal endoscope 10. At, within or near the handle 50, the working channel 31 has a bifurcation region 32. Proximal to the bifurcation region 32, the working channel 31 splits into two channels. A first portion of the working channel 31 proximal to the bifurcation regions 32 extends towards an instrument insertion port 30 suitable for, e.g., conducting a biopsy therethrough. The instrument insertion port 30 allows an instrument, e.g., a pediatric nasal endoscope biopsy forceps or other medical device, to be inserted through the bifurcation region 32 and to, and past, the distal end 40 of the endoscope shaft 20 so as to perform a procedure, e.g., a biopsy procedure, on tissue located at or near to the distal end 40 of the endoscope shaft 20.

A second portion of the working channel 31 proximal to the bifurcation regions 32 extends towards an air, water and suction (AWS) control mechanism 52. The AWS control mechanism 52 includes various valves (not shown in this view, but shown and described more fully in Applicant's co-pending U.S. patent application Ser. No. 18/108,558 filed Feb. 10, 2023, the disclosure of which is incorporated by reference herein in its entirety) that allow selective connection of the working channel 31 to the AWS tubing set 35. The AWS tubing set 35 may include one or more flexible tubes (shown and described in greater detail in Applicant's above-referenced co-pending '558 patent application). The AWS tubing set 35 may be connected to a water source 37 for supplying water through the working channel 31, to a suction source 36 for supplying suction through the working channel 31, and/or to an air source 38 for supplying air through the working channel 31, depending upon a user's selection via the AWS control mechanism 52. More specifically, the AWS control mechanism allows a user to direct one or more of air, suction or water through, e.g., the bifurcation region 32 and to, and past, the distal end 40 of the endoscope shaft 20 so as to enable their use during the performance of a procedure on tissue located at or near to the distal end 40 of the endoscope shaft 20.

The distal end 40 of the endoscope shaft 20 also includes an illumination source 42 to provide light at the distal tip 40. In embodiments, the illumination source 42 may be connected to and at least partially controllable by an electronics control module 54 located in the handle 50. The distal end 40 of the endoscope shaft 20 also includes an image capture device 44 to convey image or video signals related to the region of the distal end 40 of the endoscope shaft 20. In embodiments, the image capture device 44 may also be connected to and at least partially controllable by the electronics control module 54 located in the handle 50. The handle 50 may also include a shaft steering mechanism 56 to control or steer the lateral displacement at the distal end 40 of the endoscope shaft 20. In addition, the handle 50 may include a video display output cable 57, which may be connected to and output image data to a separate image or video display or control unit (not shown in this view).

Figure 2:
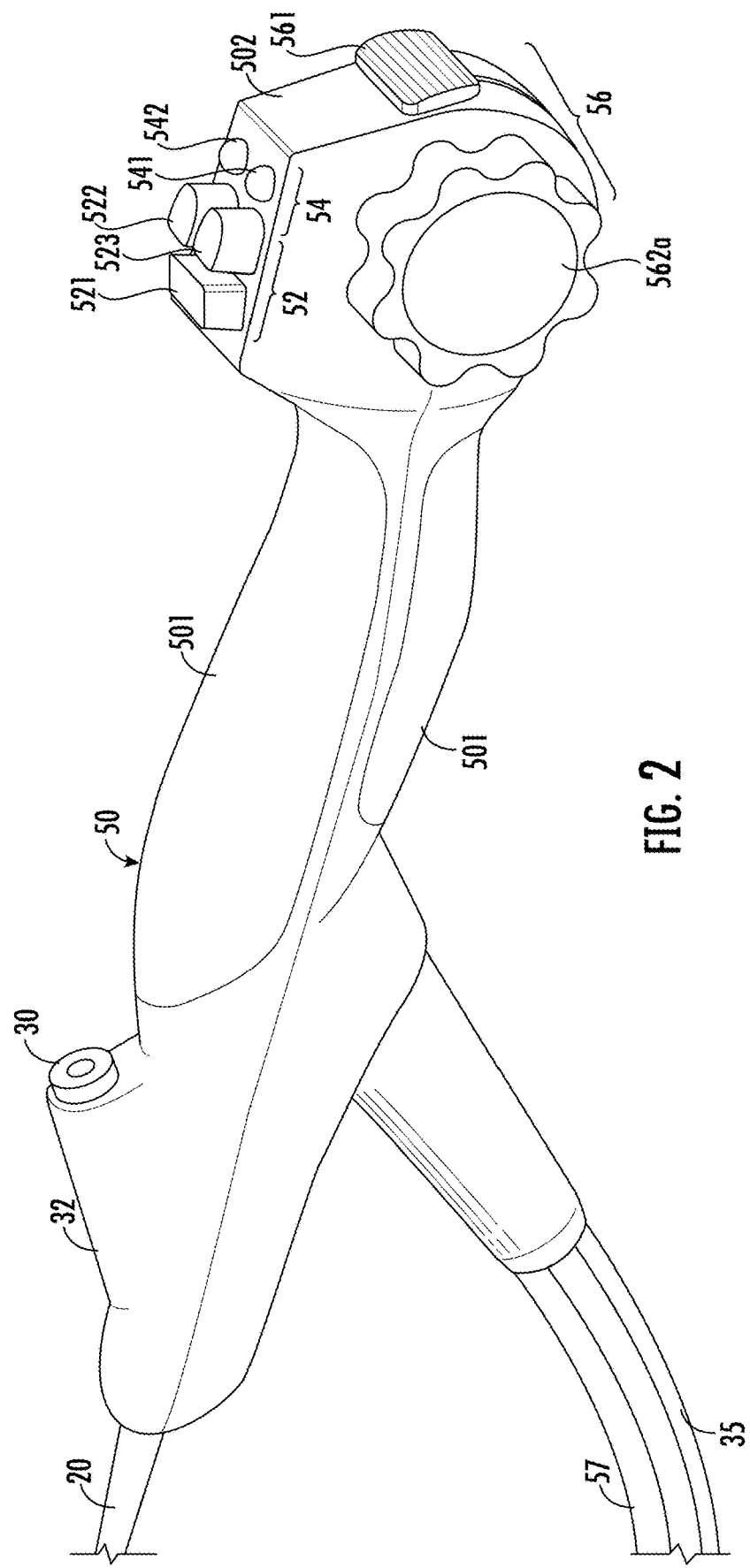
FIG. 2 is a perspective view of the handle of the trans-nasal endoscope, in accordance with various embodiments.

FIG. 2 is a perspective view of an example embodiment of the handle 50 of the trans-nasal endoscope 10. In this embodiment, the features and functionality that were shown schematically in FIG. 1 are provided in more detail, showing additional advantages thereof. For example, in this embodiment, the handle 50 of the trans-nasal endoscope 10 includes a gripping region 501 sized and contoured to fit comfortably in a user's hand. Located distally relative to the gripping region 501 is the bifurcation region 32. From the distalmost end of the bifurcation region 32 extends the flexible endoscope shaft 20, having a portion of the working channel 31 extending therethrough. The working channel 31 extends from the distal end 40 of the endoscope shaft 20, and splits into two channels in the bifurcation region 32. A first portion of the working channel 31 extends towards the instrument insertion port 30, which is suitable for receiving an instrument, e.g., a pediatric nasal endoscope biopsy forceps or other medical device, therethrough. The second portion of the working channel 31 proximal to the bifurcation region 32 extends proximally through the interior of the gripping region 501.

Proximal to the gripping region 501 is a control region 502 sized and shaped to extend beyond the heel of the user's hand when the palm of the user's hand is gripping the gripping region 501, enabling the control features positioned on the control region 502 to be engaged by the user's second hand when the user's first hand is gripping the gripping region 501.

In the embodiment shown in FIG. 2, the control region 502 has various control features positioned thereon. For example, the control region 502 has the AWS control mechanism 52. As set forth above, the AWS control mechanism 52 includes various features, e.g., buttons, valves, etc., that allow selective connection of the air, water and suction supply sources 36, 37, 38 to the working channel 31 via respective flexible tubes of the AWS tubing set 35. In the embodiment shown in FIG. 2, the AWS control mechanism 52 includes an air supply control button 521. The air supply control button 521 functions to selectively connect the air source 38 to the working channel 31, as is described in greater detail in Applicant's above-referenced co-pending '558 patent application.

In the embodiment shown in FIG. 2, the AWS control mechanism 52 also includes a water supply control button 522. The water supply control button 522 functions to selectively connect the water source 37 to the working channel 31, as is described in greater detail in Applicant's co-pending '558 patent application.

Still further, in the embodiment shown in FIG. 2, the AWS control mechanism 52 includes a suction supply control button 523. The suction supply control button 523 functions to selectively connect the suction source 36 to the working channel 31, as is described in greater detail in Applicant's co-pending '558 patent application.

In the embodiment shown in FIG. 2, the control region 502 also has the electronics control mechanism 54. As set forth above, the electronics control mechanism 54 includes various features, e.g., buttons, electrical connections, etc., that allow selective operation of, e.g, the image capture device 44 and/or the illumination device 44 located at the distal end 40 of the endoscope shaft 20. In the embodiment shown in FIG. 2, the electronics control mechanism 54 includes a first, e.g., a white balance control, button 541. In this embodiment, the white balance control button 541 functions to selectively control a white balancing operation by sending a corresponding signal to an image or video control unit (not shown), as is described in greater detail in Applicant's co-pending U.S. patent application Ser. No. 18/108,564 filed Feb. 10, 2023, the disclosure of which is incorporated by reference herein in its entirety.

In the embodiment shown in FIG. 2, the electronics control mechanism 54 also includes a second, e.g., an image capture control, button 542. In this embodiment, the image capture control button 542 functions to selectively control the capture of image or video signals sent by the image capture device 44, e.g., such as by providing a signal to an image or video display or control unit (not shown), as is described in greater detail in Applicant's above-referenced co-pending '564 patent application.

In the embodiment shown in FIG. 2, the control region 502 also has the shaft steering mechanism 56. As set forth above, the shaft steering mechanism 56 includes various features, e.g., knobs, rollers, etc., that allow a user to control or steer the lateral displacement at the distal end 40 of the endoscope shaft 20. In the embodiment shown in FIG. 2, the shaft steering mechanism 56 includes a first knob 561 for controlling a first movement of the distal end 40 of the endoscope shaft 20, as will be described in greater detail below in connection with FIG. 8. FIG. 2 also illustrates the shaft steering mechanism 56 including opposing roller knobs 562a, 562b (knob 562b being hidden from view in FIG. 2, but being located on the opposite side of the handle 50) for controlling additional movements of the distal end 40 of the endoscope shaft 20, as will be described in greater detail below in connection with FIGS. 7a and 7b.

In addition, in the embodiment shown in FIG. 2, the handle 50 of the trans-nasal endoscope 10 includes a connection to the AWS tubing set 35. As set forth above, the AWS tubing set includes various flexible tubes that connect to the suction source 36, the water source 37 and the air source 38, as is described in greater detail in Applicant's co-pending '558 patent application. Still further, the handle 50 includes a connection to a video display output 57, e.g., for connecting to and outputting image data to a separate video display or control unit (not shown in FIG. 2). In the embodiment shown in FIG. 2, the video display output 57 is bundled together with the AWS tubing set 35, as is described in greater detail in Applicant's co-pending '564 patent application.

Figure 3:
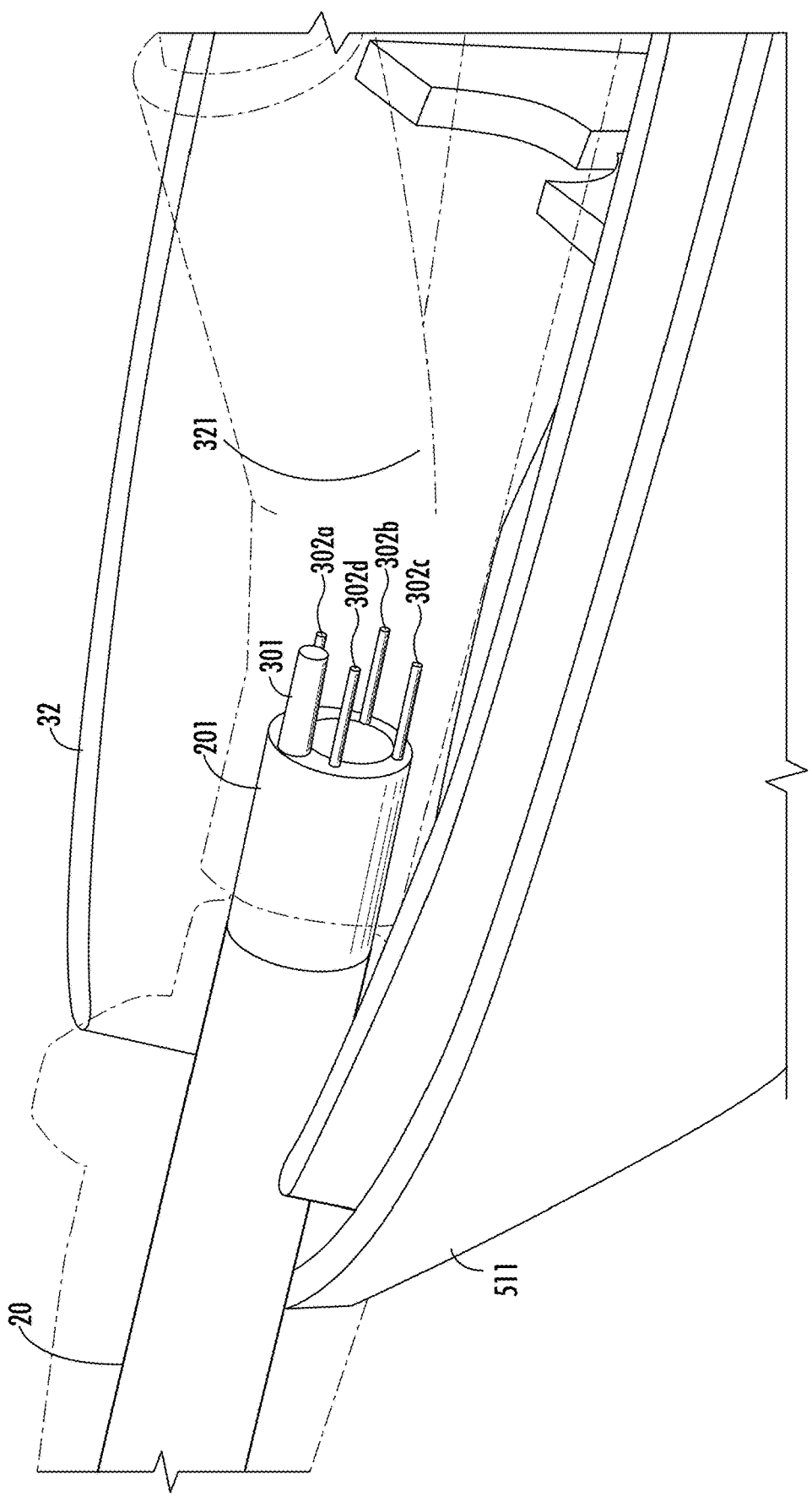
FIG. 3 is a perspective, cut-away view of a handle in the vicinity of a bifurcation region, in accordance with various embodiments.

FIG. 3 is a perspective, cut-away view of the handle 50 in the vicinity of the bifurcation region 32. In the embodiment shown in FIG. 3, the endoscope shaft 20 terminates at a location 201 that is slightly proximal relative to the distal-most end 511 of the handle 50, but also slightly distal relative to the location 321 at which the working channel 31 splits into two channels. In this embodiment, while the endoscope shaft 20 terminates at this location, it can be seen in FIG. 3 that several components that are incorporated into the endoscope shaft 20 continue to extend proximally beyond this location. Specifically, it can be seen in FIG. 3 that a camera electrical cable 301, that is embedded in, or otherwise disposed within, the wall of the endoscope shaft 20 extends proximally beyond this location towards the electronic control device 54 that is located at a more proximal location within the handle 50 (it should be noted that only a partial view of the camera electrical cable 301 is shown in FIG. 3). The camera electrical cable 301 extends longitudinally along the length of the endoscope shaft 20 so as to be parallel to the working channel 31 that is also running longitudinally through the endoscope shaft 20.

Several other components that are incorporated into the endoscope shaft 20 also continue to extend proximally beyond the location 201 and the location 321 at which the working channel 31 splits into two channels. Specifically, it can be seen in FIG. 3 that, in this embodiment, four steering wires 302a, 302b, 302c, 302d, that are embedded in, or otherwise disposed within, the wall of the endoscope shaft 20 extend proximally beyond this location towards the shaft steering mechanism 56 that is located at a more proximal location within the handle 50 (it should be noted that only a partial view of the four steering wires 302a, 302b, 302c, 302d are shown in FIG. 3). The four steering wires 302a, 302b, 302c, 302d extend longitudinally along the length of the endoscope shaft 20 so as to be parallel to the working channel 31 that is also running longitudinally through the endoscope shaft 20.

Figure 4:
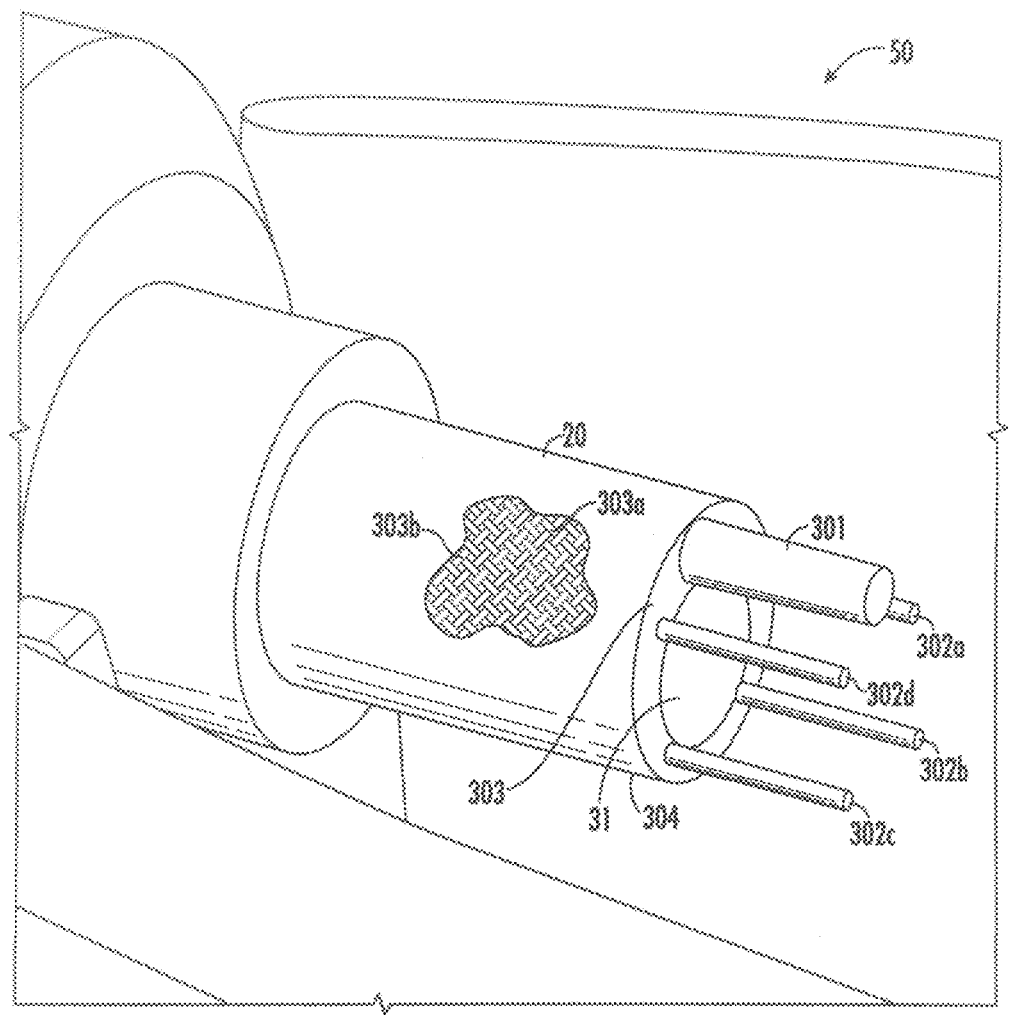
FIG. 4 is perspective, cut-away view of the handle in the vicinity of the bifurcation region, enlarged to show additional details of various components of the endoscope shaft, in accordance with various embodiments.

FIG. 4 is another perspective, cut-away view of the handle 50 in the vicinity of the bifurcation region 32, but enlarged in comparison to FIG. 3 so as to show additional details of the various components of the endoscope shaft 20. Specifically, it can be seen in FIG. 4 that the camera electrical cable 301, as well as the four steering wires 302a, 302b, 302c, 302d, are disposed within the wall of the endoscope shaft 20 so as to each be located laterally adjacent to the working channel 31. In the embodiment shown, the camera electrical cable 301 is, in the view shown, positioned at the top-most circumferential position of the endoscope shaft 20, so as to be at, e.g., a 12 o'clock or 0 degree position along the outer circumference of the working channel 31. In this embodiment, the camera electrical cable 301 maintains this same top-most circumferential position relative to the working channel 31 along the full length of the endoscope shaft 20 so as to also be in the top-most circumferential position relative to the working channel 31 at the distal end 40 of the endoscope shaft 20, where it connects to the illumination source 42 and the image capture device 44 (as is described in greater detail in Applicant's co-pending '564 patent application).

Likewise, as can be seen in FIG. 4, the four steering wires 302a, 302b, 302c, 302d are also disposed within the wall of the endoscope shaft 20 so as to each be located laterally adjacent to the working channel 31. In the embodiment shown, the four steering wires 302a, 302b, 302c, 302d are, in the view shown, positioned 90 degrees apart relative to each other, with the steering wires 302a and 302d each being spaced 45 degrees apart from the camera electrical cable 301 that is located at the top-most circumferential position of the endoscope shaft 20. For example, in this embodiment, the first steering wire 302a is located at, e.g., a 45 degree clockwise position relative to the top-most position along the outer circumference of the working channel 31. The second steering wire 302b is located at, e.g., a 135 degree clockwise position relative to the top-most position along the outer circumference of the working channel 31. The third steering wire 302c is located at, e.g., a 225 degree clockwise position relative to the top-most position along the outer circumference of the working channel 31, and the fourth steering wire 302d is located at, e.g., a 315 degree clockwise position relative to the top-most position along the outer circumference of the working channel 31. In this embodiment, the four steering wires 302a, 302b, 302c, 302d maintain their respective circumferential positions relative to the working channel 31 along the full length of the endoscope shaft 20 so as to also be in the 45, 135, 225 and 315 degree positions, respectively, relative to the working channel 31 at the distal end 40 of the endoscope shaft 20, where they connect to a steering collar (as will be shown and described in connection with FIG. 6).

Of course, it should be recognized that the endoscope shaft 20 may, in alternative embodiments, have more than one electrical cable extending longitudinally therethrough, depending on the arrangement and functionality of the illumination source and the camera componentry located at the distal end thereof. Likewise, it should be recognized that, in the embodiment shown having four steering wires extending longitudinally therethrough, these four steering wires may be circumferentially arranged within the shaft 20, and/or may be circumferentially attached to the steering collar 309, at different circumferential positions than described hereinabove, depending on the steering directions needed for a given device. An alternative arrangement of such steering wires, e.g., having the steering wires located at the 0, 90, 180 and 270 degree positions, is shown and described in connection with FIGS. 14B, 15 and 16. Still further, it should be recognized that the endoscope shaft 20 may, in still further embodiments, have more or less than four steering wires extending longitudinally therethrough, depending on the steering capability needed for a given device.

There are a variety of different manufacturing techniques that may be employed so as to embed the camera electrical cable 301 and the steering wires 302a, 302b, 302c, 302d, within the wall structure of the endoscope shaft 20, e.g., extrusion, precision molding, etc. However, these manufacturing techniques may result in the wall structure of the endoscope shaft 20 being relatively bulky or thick. As a result, the outer diameter of the endoscope shaft 20 may be undesirably large, increasing the likelihood that a patient may experience physical discomfort due to a large-diameter endoscope being inserted into the nose, through the sinus cavities and down into the esophagus. Also as a result, in order to keep the outer diameter of the endoscope shaft smaller, the thick or bulky wall structures may force the inner diameter of the working channel to be made undesirably smaller, thereby making it more difficult for instruments to be inserted into and through the working channel. Thus, traditional manufacturing techniques for the endoscope shaft may prevent the resulting endoscopes from being suitable candidates for certain procedures, e.g., pediatric trans-nasal endoscopy procedures.

The trans-nasal endoscope 10 described hereinbelow, however, according to various embodiments, provides an improved structure and method for embedding at least one wire, e.g., the camera electrical cable 301 and/or the steering wires 302a, 302b, 302c, 302d, within the wall structure of the endoscope shaft 20. According to various embodiments, the endoscope shaft 20 is manufactured using a braiding technique which weaves filaments around the working channel 31, as well as alternately over and under the camera electrical cable 301 and the steering wires 302a, 302b, 302c, 302d. As will be described in further detail below, this over/under braiding process provides an arrangement that minimizes the outer diameter of the endoscope shaft 20, e.g., to reduce the physical and mental discomfort to patients, while simultaneously maximizing the diameter of the working channel 31, e.g., to provide the largest possible channel through which tools may be introduced, all while simultaneously providing, e.g., four-way, shaft steering capabilities as well as imaging functionality.

According to embodiments, the endoscope shaft 20 is manufactured using, e.g., 16 filaments, that are woven by, e.g., 16 bobbins, around the various components of the endoscope shaft 20 via a mandrel, the mandrel travelling longitudinally along the length of the endoscope shaft 20 during its manufacture. Of course, it should be recognized that other braiding patterns, as well as other braiding or weaving equipment, may additionally or alternatively be employed in order to manufacture the endoscope shaft 20.

In the embodiment shown, in order to manufacture the endoscope shaft 20, the various components of the endoscope shaft, e.g., the camera electrical cable 301 and the four steering wires 302a, 302b, 302c, 302d, are arranged longitudinally along the length working channel 31 in, e.g., the circumferential positions described hereinabove or, in other embodiments, in other circumferential positions. In the embodiment shown herein, a given filament of the braiding structure is wound laterally over, e.g., so as to be at a position that is laterally outside of or diametrically further from the working channel 31 than, the camera electrical cable 301. This first filament is then wound laterally over, e.g., so as to be at a position that is laterally outside of or diametrically further from the working channel 31 than, the first steering wire 302a. This first filament is then wound laterally under, e.g., so as to be at a position that is laterally inside of or diametrically closer to the working channel 31 than, the second steering wire 302b, such that the first filament is positioned between the outside surface of the working channel 31 and the second steering wire 302b. This first filament is then wound laterally over, e.g., so as to be at a position that is laterally outside of or diametrically further from the working channel 31 than, the third steering wire 302c. This first filament is then wound laterally under, e.g., so as to be at a position that is laterally inside of or diametrically closer to the working channel 31 than, the fourth steering wire 302d, such that the first filament is positioned between the outside surface of the working channel 31 and the fourth steering wire 302d. This first filament is then again wound laterally over, e.g., so as to be at a position that is laterally outside of or diametrically further from the working channel 31 than, the camera electrical cable 301. In embodiments, the first filament is then woven through this same pattern repeatedly, until the first filament has reached to farthest longitudinal end of the endoscope shaft 20.

Additionally or alternatively, in the embodiment shown herein, a second given filament is wound in a different pattern, or more specifically, around the various components of the endoscope shaft 20 in a different placement, so that the collection of all filaments employed to create the braided pattern eventually fix the camera electrical cable 301, the four steering wires 302a, 302b, 302c, 302d, and the working channel in lateral and circumferential position relative to each other. For example, in the embodiment shown, a second given filament is wound laterally over, e.g., so as to be at a position that is laterally outside of or diametrically further from the working channel 31 than, the camera electrical cable 301. This second filament is then wound laterally under, e.g., so as to be at a position that is laterally inside of or diametrically closer to the working channel 31 than, the first steering wire 302a, such that the second filament is positioned between the outside surface of the working channel 31 and the first steering wire 302a. This second filament is then wound laterally over, e.g., so as to be at a position that is laterally outside of or diametrically further from the working channel 31 than, the second steering wire 302b. This second filament is then wound laterally under, e.g., so as to be at a position that is laterally inside of or diametrically closer to the working channel 31 than, the third steering wire 302c, such that the second filament is positioned between the outside surface of the working channel 31 and the third steering wire 302c. This second filament is then wound laterally over, e.g., so as to be at a position that is laterally outside of or diametrically further from the working channel 31 than, the fourth steering wire 302d. This second filament is then again wound laterally over, e.g., so as to be at a position that is laterally outside of or diametrically further from the working channel 31 than, the camera electrical cable 301.

Advantageously, the various filaments that comprise the braided structure of the endoscope shaft 20 are each woven around the working channel 31 and the other components of the endoscope shaft 20 in a pattern. In an embodiment, the various filaments that comprise the braided structure of the endoscope shaft 20 are alternatingly woven in the two patterns described hereinabove. For example, in such an embodiment, the first, third, fifth, etc. filaments are woven in the first above-described pattern, while the alternating filaments, e.g., the second, fourth, sixth, etc. filaments, are woven in the second above-described pattern. Employing different weaving patterns for different filaments, e.g., such as by alternating them as described herein above such that some filaments are woven over and some filaments are woven under each of the electrical cable and/or the steering wires, improves the stability of the endoscope shaft 20 while simultaneously minimizing the wall thickness of the endoscope shaft 20, and thereby minimizing the outer diameter of the endoscope shaft 20. Of course, it should be recognized that other weaving patterns other than those described above may be employed, and the filaments employed to create the braided structure of the endoscope shaft 20 may be woven in a different arrangement or order than described hereinabove.

It should also be recognized that, while the braiding patterns set forth hereinabove were described as having the first filament engage the camera electrical cable 301 first, e.g., starting at a 12 o'clock or 0 degree circumferential position, this is merely exemplary. Other starting points, other than over the camera electrical cable 301, and at different circumferential positions, are also contemplated. For example, while the braiding patterns set forth above describe a first filament starting to be woven from over the camera electrical cable 301, e.g., from a 12 o'clock or 0 degree circumferential position, the other filaments in that same braiding pattern would start to be woven at different circumferential positions depending, e.g., on the number of filaments employed in that particular braiding pattern. By way of example, in a braiding pattern that employs, e.g., 16 filaments, to create its woven pattern, each filament could start its respective pattern equidistantly around the circumference of the endoscope shaft 20, e.g., a first filament starting its respective weaving pattern at a 0 degree circumferential position, a second filament starting its respective weaving pattern at a 22.5 degree circumferential position, etc. Of course, any such braiding pattern or filament spacing may be employed to minimize the wall thickness of the endoscope shaft 20 and thereby minimize the outer diameter thereof.

FIG. 4 also illustrates that, disposed around the filament 303a, 303b, etc., collectively the braided filaments 303, is a laminate layer 304. The laminate layer 304 may have various different functions. For example, the laminate layer 304 may function to protect the braided filaments 303, e.g., from breakage due to contact with sharp or other potentially physically damaging elements. The laminate layer 304 may also function to protect the internal components of the endoscope shaft 20, e.g., particularly the camera electrical cable 301 and the illumination source and imagine device, from damage due to, e.g., moisture.

Advantageously, according to various embodiments, the endoscope shaft 20 may provide different amounts of flexibility along its longitudinal length. In embodiments, the endoscope shaft 20 described herein provides such different amounts of flexibility along its longitudinal length by having, along its longitudinal length, sections for which the laminate layer 304 has different characteristics. For example, the endoscope shaft 20 described herein may provide such different amounts of flexibility along its longitudinal length by having sections for which the laminate layer 304 has different flexibilities/rigidities. Alternatively, and as shown and described in connection with the FIGS. 14B, 15 and 16, the endoscope shaft may provide the same amount of flexibility along nearly its entire longitudinal length, such flexibility being significantly improved by the design therein of having the steering wires embedded within a braid structure in the shaft wall wherein the steering wires are located at the 0, 90, 180 and 270 degrees coordinates.

Figure 5:
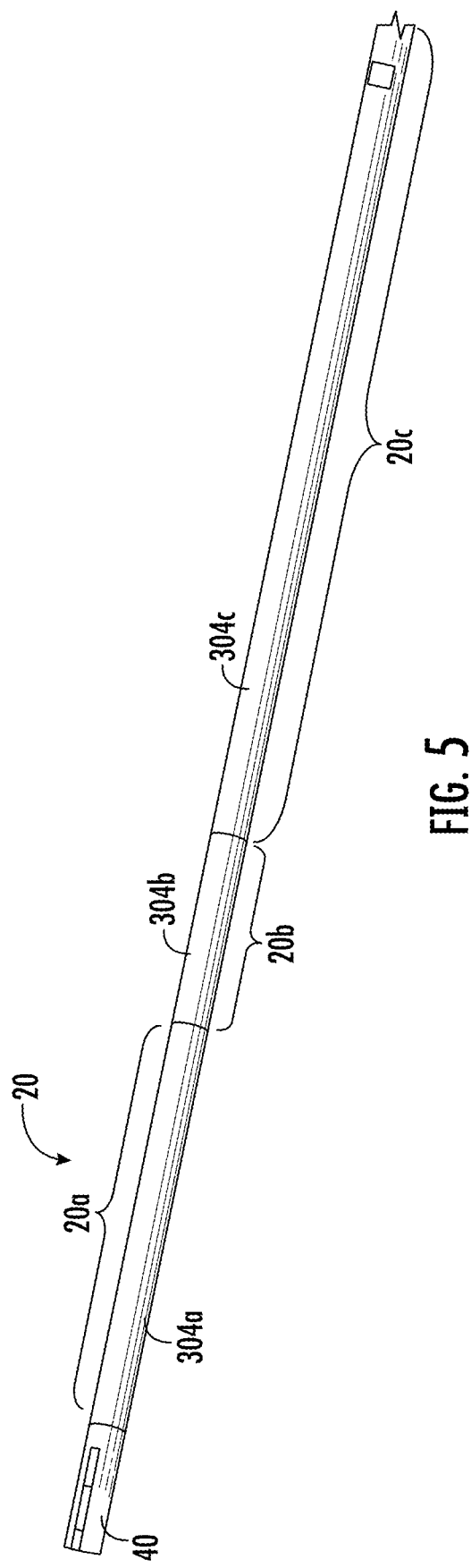
FIG. 5 illustrates an endoscope shaft having different types of laminate layer, in accordance with various embodiments.

Returning back to the varied flexibility version shown in FIG. 5, in such an embodiment, the endoscope shaft 20 may have a section near its distal end 44 for which the laminate layer 304 is relatively flexible relative to the other longitudinal sections of the endoscope shaft 20, thereby imparting additional flexibility to this longitudinal section of the endoscope shaft 20. This increased relative flexibility of the longitudinal section near the distal end 44 could enable the distal end 44 of the endoscope shaft 20 to be better steered, e.g., by the shaft steering mechanism 56 and the steering wires 302a, 302b, 302c, 302d, more easily by a user. Additionally or alternatively, in an embodiment, the endoscope shaft 20 may have a section nearer to its handle 50 for which the laminate layer 304 is relatively more rigid relative to the other, e.g., distal, longitudinal sections of the endoscope shaft 20, thereby imparting additional rigidity to this longitudinal section of the endoscope shaft 20. This increased relative rigidity of the section nearer to the handle 50 could enable the more proximal end of the endoscope shaft 20 to more easily maintain its shape during use.

The endoscope shaft 20 having different amounts of flexibility along its longitudinal length may be beneficial for several reasons. For example, and as set forth above, transnasal endoscopy procedures require an endoscope shaft to be inserted into the nasal passages of a patient, through the patient's sinus cavities and down into the patient's esophagus. This path is winding and curved and is lined with the patient's sensitive tissues, traditionally resulting in an undesirably high likelihood that an endoscope shaft inserted therethrough could detrimentally irritate or injure the patient. This discomfort to the patient also increases the likelihood that a patient would discontinue a procedure that has already begun, and/or the expectation of discomfort could cause a patient to avoid the procedure altogether. Knowing or anticipating the patient's discomfort, the surgeon may also experience increased anxiety and/or it may potentially negatively impact the surgeon's performance of the procedure. By increasing the relative flexibility of the endoscope shaft 20 at or near to its distal end 44 and thereby rendering the distal end 44 more steerable, a surgeon may be able to decrease the likelihood that the distal end 44 irritates or injures the patient's soft tissues when the distal end 44 of the endoscope 20 is being introduced into the patient's nasal cavity and is being maneuvered through the winding path within the patient. Additionally or alternatively, by increasing the relative rigidity of the endoscope shaft 20 at or nearer to its handle 50 and thereby rendering the proximal end of the endoscope shaft 20 more stable, a surgeon may be able to decrease the likelihood that the proximal end of the endoscope shaft 20 moves and thereby irritates or injures the patient's soft tissues when the endoscope shaft 20 is in position within the patient's nasal cavity etc. Still further, by increasing the relative rigidity of the endoscope shaft 20 at or nearer to its handle 50 and thereby rendering the proximal end of the endoscope shaft 20 more stable, a surgeon may be better able to feed the endoscope shaft 20 into the patient's nasal cavity without the proximal end of the endoscope shaft 20 collapsing or undesirably bending, thereby improving the ability for the endoscope shaft 20 to be controlled during insertion.

Accordingly, in various embodiments, the endoscope shaft 20 described herein may employ two or more different types of laminate layer 304 at different longitudinal sections thereof. FIG. 5 illustrates an example embodiment in which the endoscope shaft 20 described herein may employ three different types of laminate layer 304 at different longitudinal sections thereof. Specifically, FIG. 5 illustrates a first laminate layer 304a which envelops a first, e.g., distal, endoscope shaft section 20a that is adjacent to or near a distal end 44 of the endoscope shaft 20. In addition, FIG. 5 illustrates a second laminate layer 304b which envelops a second, e.g., central, endoscope shaft section 20b that is proximal relative to the first endoscope section 20a of the endoscope shaft 20. Still further, FIG. 5 illustrates a third laminate layer 304c which envelops a third, e.g., proximal, endoscope shaft section 20a that is proximal relative to the second endoscope section 20b of the endoscope shaft 20 and adjacent to or near the handle 50 (not shown).

In this embodiment, the first laminate layer 304a may comprise a relatively flexible polymer (flexibility being measurable by any commonly employed test for same, e.g., elastic modulus or Young's modulus, as is well known by persons of skill in the art). For example, the first laminate layer 304a may comprise, e.g., Pebax® 35D (Pebax® being a tradename for a thermoplastic elastomer of polyether block amide, obtained by, e.g. polycondensation of a carboxylic acid polyamide with an alcohol termination polyether, available commercially from, e.g., Compounding Solutions in Lewiston, ME). By enveloping the first endoscope shaft section 20a with a first laminate layer 304a that is comprised of a relatively flexible polymer such as Pebax® 35D, the first endoscope shaft section 20a may enable that section of the endoscope shaft 20 to be more easily steered by a user.

In this embodiment, the second laminate layer 304b may comprise a polymer that is still flexible but is somewhat less flexible than the first laminate layer 304a. For example, the second laminate layer 304b may comprise, e.g., Pebax® 55D. By enveloping the second endoscope shaft section 20b with a second laminate layer 304b that is comprised of a lesser flexible polymer such as Pebax® 55D, the second endoscope shaft section 20b may enable that section of the endoscope shaft 20 to still be bendable as it travels through the patient's various soft tissues, but also enables it to be more stable so it can be fed into the patient's nasal cavity by a user without undesirably collapsing or sagging.

Still further, in this embodiment, the third laminate layer 304c may comprise a polymer that is again still flexible but is somewhat less flexible still than the second laminate layer 304b. For example, the third laminate layer 304c may comprise, e.g., Pebax® 72D or a suitable polyimide. By enveloping the third endoscope shaft section 20c with a third laminate layer 304c that is comprised of a still less flexible polymer such as Pebax® 72D or polyimide, the third endoscope shaft section 20c may enable that section of the endoscope shaft 20 to still be somewhat bendable if it were to travel through the patient's various soft tissues, but also enables it to be even more stable so, as it is used to feed the more distal sections of the endoscope shaft 20 into the patient's nasal cavity, the third endscope shaft section 20c is rigid enough to be pushed on by a user without it collapsing or sagging. Of course, the endoscope 10 may have more than three longitudinal sections, depending on the degrees of varying flexibility needed along the length of the endoscope shaft 20.

As set forth above, the endoscope shaft 20 may provide different amounts of flexibility along its longitudinal length, for example a section near its distal end 44 that is relatively more flexible to enable the distal end 44 of the endoscope shaft 20 to be better steered, and a section nearer to its handle 50 that is relatively more rigid to enable the more proximal end of the endoscope shaft 20 to more easily maintain its shape during use. Additionally or alternatively, the endoscope shaft 20 may provide still additional differing amounts of flexibility along its longitudinal length, such as providing a relatively more flexible zone nearer to the handle 50 so as to provide a patient comfort zone.

Figure 9:
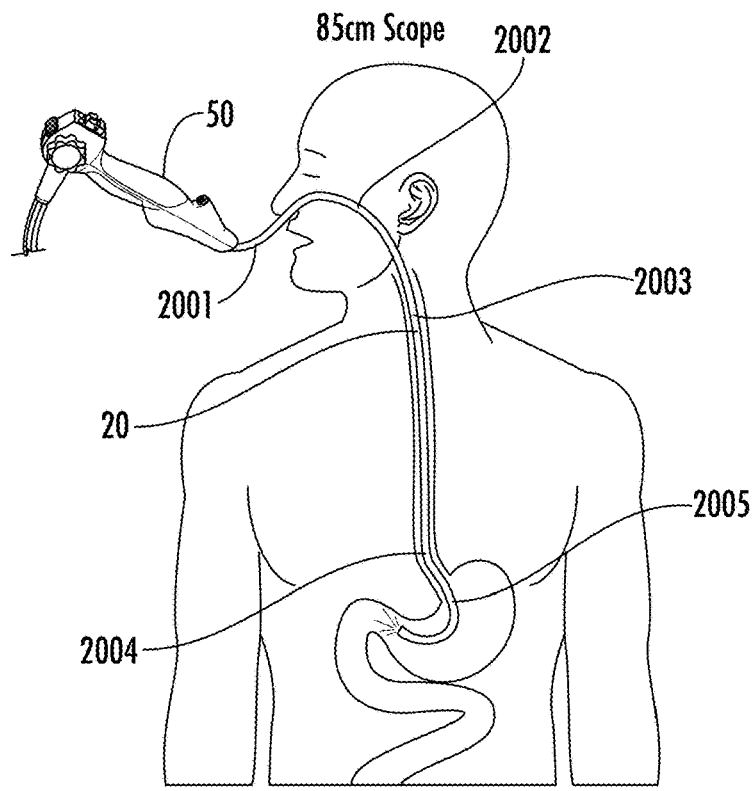
FIG. 9 illustrates an endoscope shaft configured to reach a patient's stomach and having a patient comfort zone that resides in the patient's nasal cavity when the shaft is fully inserted, in accordance with various embodiments.

For example, in the embodiment shown in FIG. 9, there is shown an endoscope 10 for use in a surgical procedure that comprises a handle 50 for gripping by a user and a shaft 20 extending from the handle 50. As set forth above, the shaft 20 may have a working channel (not shown in FIG. 9, but see, e.g., working channel 31 in preceding figures) extending longitudinally therethrough. The shaft 20 is configured to be longitudinally inserted into a nasal opening of a patient until the shaft 20 reaches a fully-inserted position within the patient, e.g., a position at which the distal end 40 of the shaft 20 has reached its intended insertion location and is not intended to be inserted any further. In the embodiment shown, the shaft 20 has a length of about 85 cm.

As shown in FIG. 9, when the shaft 20 is in the fully-inserted position, the shaft 20 may have an extracorporeal zone 2001. The extracorporeal zone 2001 may be configured to reside proximal relative to the patient's nasal opening. In addition, the extracorporeal zone 2001 may have a first flexibility that is relatively more rigid so as to enable better handling by the surgeon and prevent sagging or excessive bending when the surgeon is handling the shaft 20.

As set forth above, and as shown in FIG. 9, the shaft 20 may also have a patient comfort zone 2002. The patient comfort zone 2002 may extend distally from the extracorporeal zone 2001. When the shaft 20 is in the fully-inserted position, the patient comfort zone 2002 may be configured to reside from the patient's nose through the patient's pharynx and to a top of the patient's esophagus. The patient comfort zone 2002 may have a second flexibility that is more flexible than the flexibility of the extracorporeal zone 2001. Advantageously, the patient comfort zone 2002 has a flexibility that enable sit to be comfortable to a patient when the shaft 20 is positioned at the fully-inserted position.

Still further, and as shown in FIG. 9, the shaft 20 may also have an esophageal working zone 2003. The esophageal working zone 2003 may extend distally from the patient comfort zone 2002. When the shaft 20 is in the fully-inserted position, the esophageal working zone 2003 may be configured to reside from the top of the patient's esophagus to a top of the patient's stomach. Advantageously, the esophageal working zone 2003 may have a third flexibility that is less flexible than the flexibility of the patient comfort zone 2002, since once the shaft 20 is in the fully-inserted position, the esophagus of the patient is relatively straight and thus may require less flexibility in order to be comfortable to the patient.

Still further, and as shown in FIG. 9, the shaft 20 may also have a distal flex zone 2004. The distal flex zone 2004 may extend distally from the esophageal working zone 2003. The distal flex zone 2004 may have a fourth flexibility that is more flexible than the esophageal working zone 2003, since this is the zone that is initially steered through the curvatures of the patient's nasal cavity.

Still further, and as shown in FIG. 9, the shaft 20 may also have a distal tip 2005. The distal tip 2005 may extend distally from the distal flex zone 2004 and may include an electronic component (such as the camera and/or illumination source referenced hereinabove) so as to provide image and/or video signals of the desired location in the patient when the shaft 20 is in the fully-inserted position.

As discussed previously, the relative flexibilities and/or rigidities of the various aforementioned zones of the shaft 20 may be accomplished, e.g., by each such zone having a laminate layer of differing materials or having a different number of braid per linear inch.

As set forth above, in various embodiments, the shaft 20 may have a length of about 85 cm. In such an embodiment, the various zones may have different individual lengths, depending on the size of the patient, the layout of the surgical space, the preferences of the surgeon, among various other factors. By way of example, in one such embodiment in which the shaft 20 has a length of about 85 cm, the extracorporeal zone may have a length of about 25 cm, the patient comfort zone may have a length of about 30 cm, the esophageal working zone may have a length of about 23 cm, the distal flex zone may have a length of about 6 cm, and the distal tip may have a length of about 1 cm. While these particular lengths are exemplary, they coincide roughly with the lengths of the relevant anatomical structures within a typical patient, although different lengths may be employed to accommodate patients of different sizes, e.g., pediatric, adult, etc.

Figure 10:
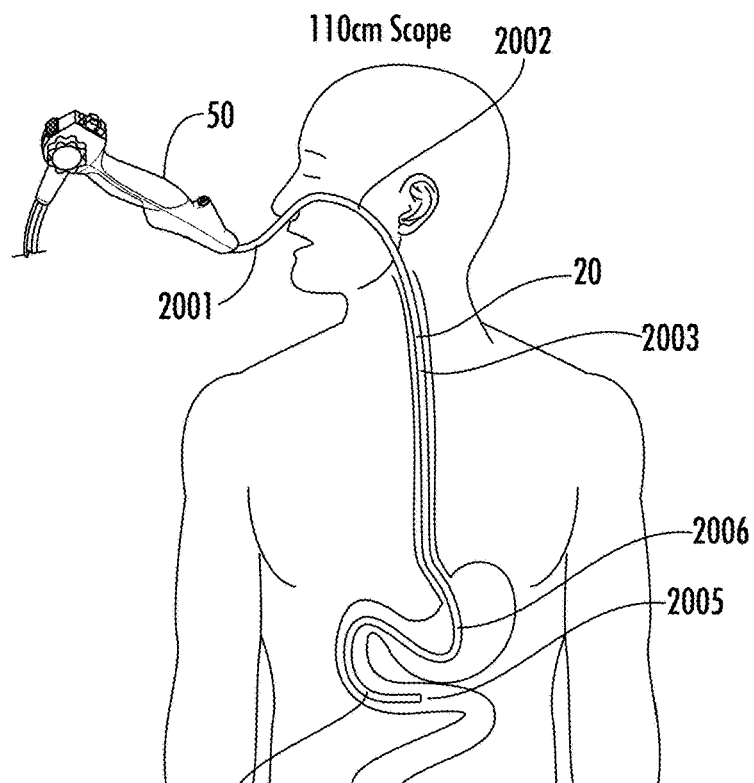
FIG. 10 illustrates an endoscope shaft configured to reach beyond a patient's stomach and having a patient comfort zone that resides in the patient's nasal cavity when the shaft is fully inserted, in accordance with various embodiments.

In still another example, e.g., the embodiment shown in FIG. 10, there is shown an endoscope 10 for use in a surgical procedure that has a longer length, e.g., 110 cm, so as to enable the surgeon to reach further regions of the patient's anatomy. In the embodiment shown in FIG. 10, the endoscope 10 includes a handle 50 for gripping by a user and a shaft 20 extending from the handle 50. As set forth above, the shaft 20 may have a working channel (not shown in FIG. 10, but see, e.g., working channel 31 in preceding figures) extending longitudinally therethrough. The shaft 20 is configured to be longitudinally inserted into a nasal opening of a patient until the shaft 20 reaches a fully-inserted position within the patient, e.g., a position at which the distal end 40 of the shaft 20 has reached its intended insertion location and is not intended to be inserted any further.

As shown in FIG. 10, when the shaft 20 is in the fully-inserted position, the shaft 20 may have an extracorporeal zone 2001. As described above on connection with FIG. 9, the extracorporeal zone 2001 may be configured to reside proximal relative to the patient's nasal opening. In addition, the extracorporeal zone 2001 may have a first flexibility that is relatively more rigid so as to enable better handling by the surgeon and prevent sagging or excessive bending when the surgeon is handling the shaft 20.

As set forth above, and as shown in FIG. 10, the shaft 20 may also have a patient comfort zone 2002. The patient comfort zone 2002 may extend distally from the extracorporeal zone 2001. As described above, when the shaft 20 is in the fully-inserted position, the patient comfort zone 2002 may be configured to reside from the patient's nose through the patient's pharynx and to a top of the patient's esophagus. The patient comfort zone 2002 may have a second flexibility that is more flexible than the flexibility of the extracorporeal zone 2001. Advantageously, and similar to FIG. 9, the patient comfort zone 2002 has a flexibility that enables it to be comfortable to a patient when the shaft 20 is positioned at the fully-inserted position.

Still further, and as shown in FIG. 10, the shaft 20 may also have an esophageal working zone 2003. The esophageal working zone 2003 may extend distally from the patient comfort zone 2002. As above, when the shaft 20 is in the fully-inserted position, the esophageal working zone 2003 may be configured to reside from the top of the patient's esophagus to a top of the patient's stomach. Advantageously, the esophageal working zone 2003 may have a third flexibility that is less flexible than the flexibility of the patient comfort zone 2002, since once the shaft 20 is in the fully-inserted position, the esophagus of the patient is relatively straight and thus may require less flexibility in order to be comfortable to the patient.

Still further, and as shown in FIG. 10, the shaft 20 may also have a stomach working zone 2006. The stomach working zone 2006 may extend distally from the esophageal working zone 2003. Advantageously, when the shaft 20 is in the fully-inserted position, the stomach working zone 2006 is configured to reside within the patient's stomach, and my also have a flexibility suitable for remaining in the patient's stomach without causing undue discomfort to the patient.

Still further, and as shown in FIG. 10, the shaft 20 may also have a distal flex zone 2004. The distal flex zone 2004 may extend distally from the stomach working zone 2006. The distal flex zone 2004 may have a fourth flexibility that is more flexible than the esophageal working zone 2003, since this is the zone that is initially steered through the curvatures of the patient's nasal cavity.

Still further, and as shown in FIG. 10, the shaft 20 may also have a distal tip 2005. The distal tip 2005 may extend distally from the distal flex zone 2004 and may include an electronic component (such as the camera and/or illumination source referenced hereinabove) so as to provide image and/or video signals of the desired location in the patient, e.g., the patient's intestines, when the shaft 20 is in the fully-inserted position.

As discussed previously, the relative flexibilities and/or rigidities of the various aforementioned zones of the shaft 20 may be accomplished, e.g., by each such zone having a laminate layer of differing materials or having a different number of braids per linear inch.

As set forth above, in various embodiments, the shaft 20 of FIG. 10 may have a length of about 110 cm. In such an embodiment, the various zones may have different individual lengths, depending on the size of the patient, the layout of the surgical space, the preferences of the surgeon, among various other factors. By way of example, in one such embodiment in which the shaft 20 has a length of about 110 cm, the extracorporeal zone may have a length of about 25 cm, the patient comfort zone may have a length of about 30 cm, the esophageal working zone may have a length of about 23 cm, the stomach working zone may have a length of about 25 cm, the distal flex zone may have a length of about 6 cm, and the distal tip may have a length of about 1 cm. Again, while these particular lengths are exemplary, they coincide roughly with the lengths of the relevant anatomical structures within a typical patient, although different lengths may be employed to accommodate patients of different sizes, e.g., pediatric, adult, etc.

Figure 6:
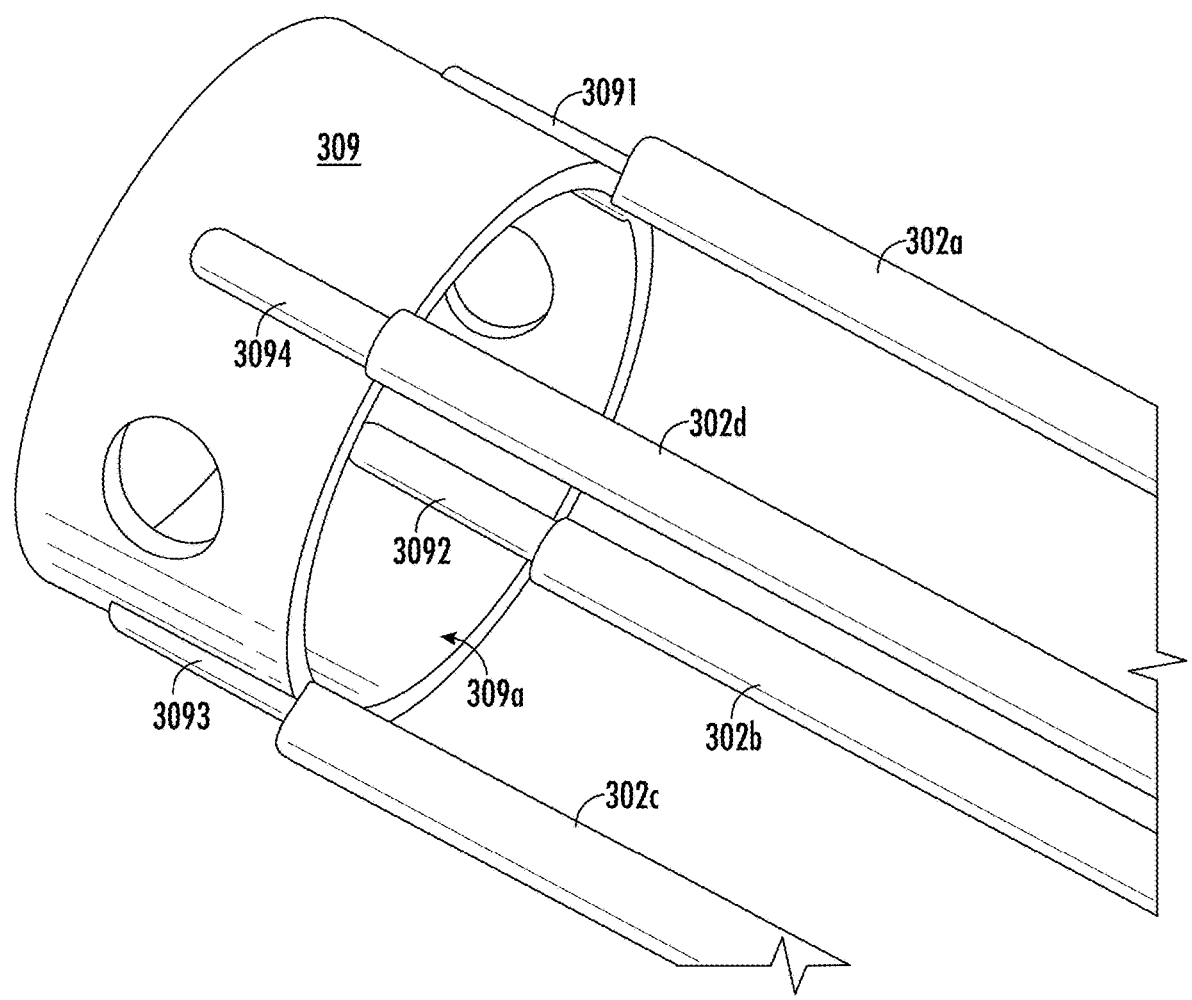
FIG. 6 illustrates a steering collar, in accordance with various embodiments.

As set forth above, the handle 50 may include a shaft steering mechanism 56 to control the lateral displacement at the distal end 40 of the endoscope shaft 20. In the embodiment shown in FIG. 4, the handle 50 includes four steering wires 302a, 302b, 302c, 302d disposed within the wall of the endoscope shaft 20 and positioned 90 degrees apart relative to each other. FIG. 6 illustrates an example embodiment of a steering collar 309. The steering collar 309 may be configured with, e.g., a ring-like structure. The steering collar 309 may be embedded within the wall of the endoscope shaft 20, e.g., it may be enclosed in the wall of the endoscope shaft 20 by having the braiding filaments woven therearound.

The steering collar 309 has an interior opening 309a through which the working channel 31 passes. In addition, the steering collar 309 may have various connection points at which the various steering wires are connected. For example, in the embodiment shown, the steering collar 309 has a first connection point 3091 for the first steering wire 302a. The first connection point 3091 is located at, e.g., a 45 degree clockwise position relative to the top-most position along the outer circumference of the working channel 31. Thus, the first connection point 3091 is advantageously located at a circumferential position relative to the working channel 31 that is the same as the circumferential position of the first steering wire 302a as it extends along the full length of the endoscope shaft 20.

In the embodiment shown, the steering collar 309 also has second, third, and fourth connection points 3092, 3093, and 3094 for connecting the steering collar 309 to the second, third and fourth steering wires 302b, 302c and 302d, respectively. The second, third, and fourth connection points 3092, 3093, and 3094 are located at, e.g., 135, 225 and 315 degree clockwise circumferential positions, respectively, relative to the top-most position along the outer circumference of the working channel 31. Thus, the second, third, and fourth connection points 3092, 3093, and 3094 are advantageously located at respective circumferential positions relative to the working channel 31 that are the same as the respective circumferential positions of the second, third and fourth steering wires 302b, 302c, 302d as they extend along the full length of the endoscope shaft 20.

The opposite ends of the steering wires 302a, 302b, 302c, 302d pass through the handle 50 and are connected to the shaft steering mechanism 56. Specifically, in the embodiment described hereinabove, the opposite, e.g., proximal, ends of the steering wires 302a, 302b, 302c, 302d pass through the distal end of the handle 50 and are connected to steering structures located within the proximal end of the handle 50. Each of the steering structures are connected to one or more of the first knob 561 and/or the opposing roller knobs 562a, 562b, which enable a user to actuate the internal steering structures and thereby move, e.g., pull, the steering wires 302a, 302b, 302c, 302d for controlling movements of the distal end 40 of the endoscope shaft 20.

Figure 7A:
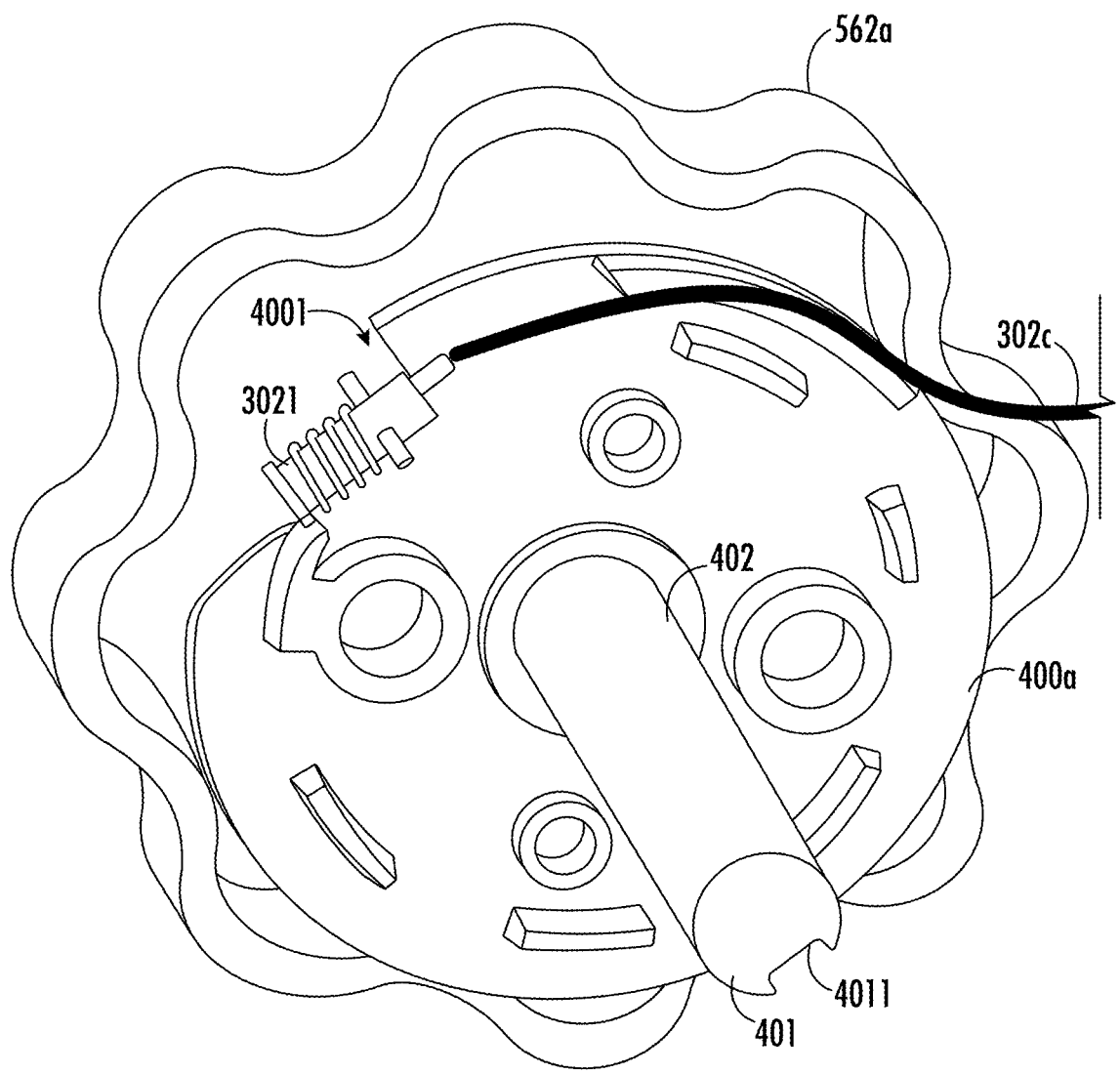
FIG. 7a is a perspective view from one side of the handle, in accordance with various embodiments.
Figure 7B:
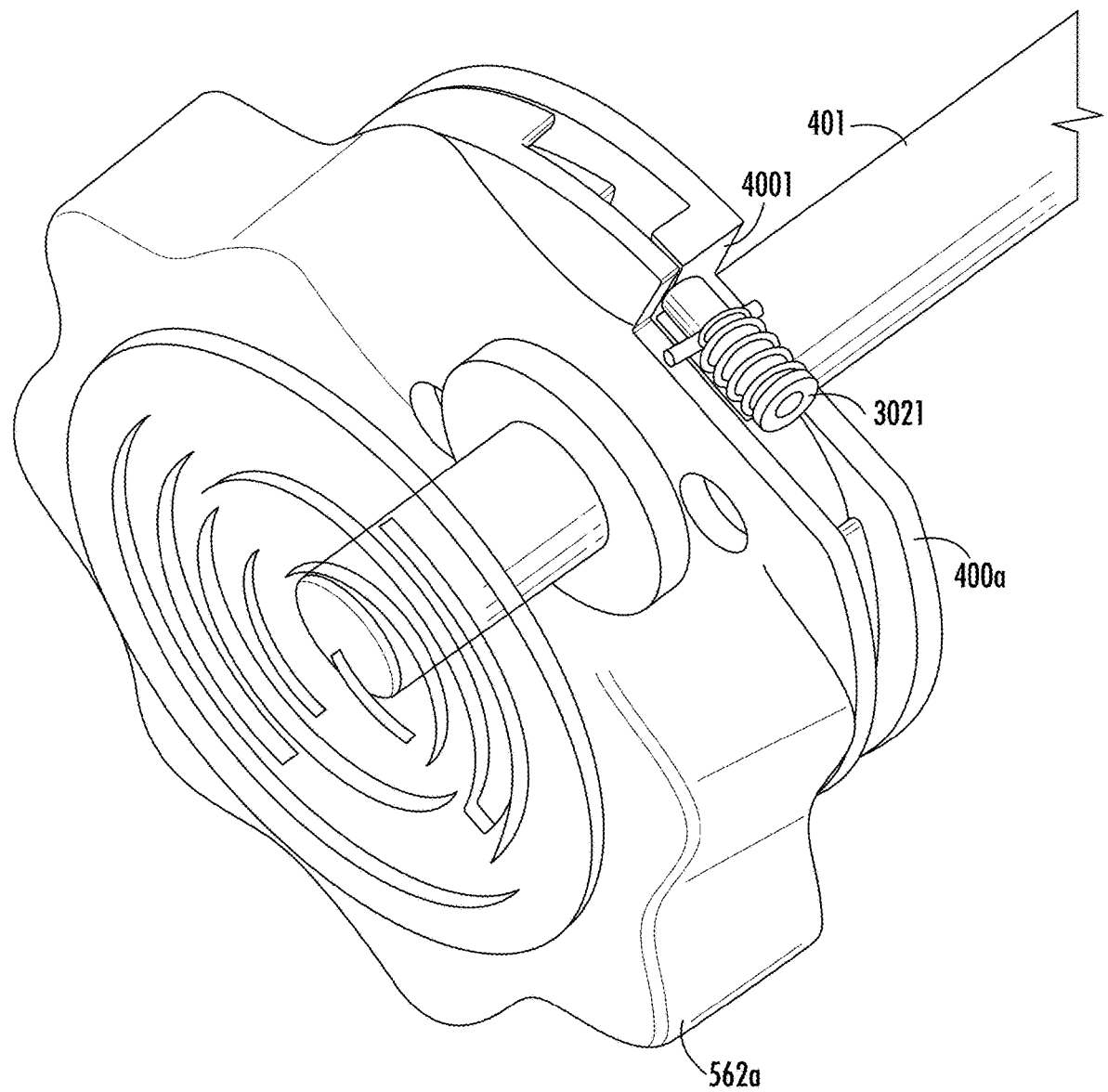
FIG. 7b is a perspective view from the opposite side of the handle, in accordance with various embodiments.

FIGS. 7a and 7b are partial perspective views (with most of the handle 50 and associated structures hidden so as not to obscure the view of various steering structures) that illustrate an example embodiment of an internal steering structure. FIG. 7a is a perspective view from one side of the handle 50, while FIG. 7b is a perspective view from the opposite side of the handle 50. Referring to FIG. 7a, there is shown a first internal steering structure in the form of a first roller wheel 400a. The first roller wheel 400a resides within the interior of the handle 50 and is generally adjacent to the inside surface of the wall of the handle 50 (the wall of the handle 50 being hidden in this view). FIG. 7a also shows a first roller knob 562a. The first roller knob 562a resides outside of the wall of the handle 50 and is generally adjacent to the outside surface of the side wall of the handle 50 (again, the wall of the handle 50 being hidden in this view).

Although not shown in these views (so as not to obscure the view of the first set of steering structures), the shaft steering mechanism 56 of the trans-nasal endoscope 10, according to various embodiments, may also include a second set of steering structures. In the trans-nasal endoscope 10 shown and described hereinabove, the second set of steering structures may be mirror images of the first roller wheel 400a and the first roller knob 562a. Specifically, the shaft steering mechanism 56 may include a second roller wheel which is located on the opposite side of the handle 50 as compared to the first roller wheel 400a, the second roller wheel also residing within the interior of the handle 50 and being generally adjacent to the inside surface of the opposite wall of the handle 50. In addition, the shaft steering mechanism 56 may also include a second roller knob 562b which is located on the opposite side of the handle relative to the first roller knob 562a, the second roller knob also residing outside of the handle 50 and being generally adjacent to the outside surface of the opposite wall of the handle 50.

It should be understood that, because the first and second steering structures, in the embodiment shown herein, are mirror images of each other, the features of the first steering structure have symmetrical features in the second steering structure. Having the first and second steering structures be symmetrical, e.g., and on opposite sides of the handle 50 relative to each other, enables ambidextrous operation of these steering structures. Furthermore, because the first and second steering structures are mirror images of each other, the operation of the first steering structure may result in simultaneous and symmetrical operation of the second steering structure, and vice versa. Thus, for the purposes of illustration, the features and operation of the first steering structures, e.g., the first roller wheel 400*a* and the first roller knob 562*a*, will be described below, recognizing that such features and operations may result in similar operation of the second steering structures, e.g., the second roller wheel and the second roller knob.

Referring again to FIGS. 7*a* and 7*b*, the roller wheel 400*a* defines an opening 402*a* at its center. A shaft 401 resides within the opening 402*a* of the roller wheel 400*a*. The shaft 401 extends laterally through both sides of the handle 50 (not shown in this view), such that a first end of the shaft 401 is connected to the first roller knob 562*a* as shown in FIG. 7*a*, while the second end of the shaft 401 is connected to the second roller knob (which is hidden in this view). In this embodiment, the shaft 401 has a key feature 4011 which mates with corresponding key features (not shown) on the first roller wheel 400*a* and the first roller knob 562*a* (likewise, though not shown in this view, the key feature 4011 of the shaft 401 may also mate with corresponding key features on the second roller wheel and the second roller knob). In this way, rotation by a user of the first roller knob 562*a* causes the shaft 401 to rotate, which thereby also causes the first roller wheel 400*a*, the second roller wheel and the second roller knob to also rotate. Likewise, because they are all keyed to the shaft 401, rotation by a user of the second roller knob also causes the second roller wheel, the first roller wheel 400*a* and the first roller knob 562*a* to also rotate.

In the embodiment shown, each of the first and second roller wheels has a respective steering wire attached thereto. For example, as shown in FIG. 7*a*, the first roller wheel 400*a* is connected to the proximal end of the third steering wire 302*c*. More specifically, the proximal end of the third steering wire 302*c* has a crimp 3021 which fixedly attaches it into a slot 4001 on the outer circumference of the first roller wheel 400*a*. Thus, rotation by a user of the first roller knob 562*a* causes rotation of the first roller wheel 400*a*, which in turn causes the proximal end of the third steering wire 302*c* to be pulled. Pulling the proximal end of the third steering wire 302*c* causes the length of the third steering wire 302*c* to move proximally within the shaft wall and thereby cause the steering collar 309 to move proximally at the circumferential position at which the third steering wire 302*c* is connected. In the embodiment shown, this proximal movement of the third steering wire 302*c* pulls the left side of the steering collar 309 such that the distal end 44 of the endoscope shaft 20 is steered towards the left.

As set forth above, the second set of steering structures, e.g., the second roller knob and the second roller wheel may be mirror images of the first roller wheel 400*a* and the first roller knob 562*a*. Thus, although hidden from view in FIG. 7*a*, the second roller wheel may be connected to the proximal end of its own corresponding steering wire, e.g., the first steering wire 302*a*. More specifically, the proximal end of the first steering wire 302*a* may have a similar crimp which fixedly attaches it into a slot on the outer circumference of the second roller wheel. In this way, rotation by a user of the second roller knob causes rotation of the second roller wheel, which in turn causes the proximal end of the first steering wire 302*a* to be pulled. Pulling the proximal end of the first steering wire 302*a* causes the length of the first steering wire 302*a* to move proximally within the shaft wall and thereby cause the steering collar 309 to move proximally at the circumferential position at which the first steering wire 302*a* is connected. In the embodiment shown, this proximal movement of the first steering wire 302*a* pulls the right side of the steering collar 309 such that the distal end 44 of the endoscope shaft 20 is steered towards the right.

Figure 8:
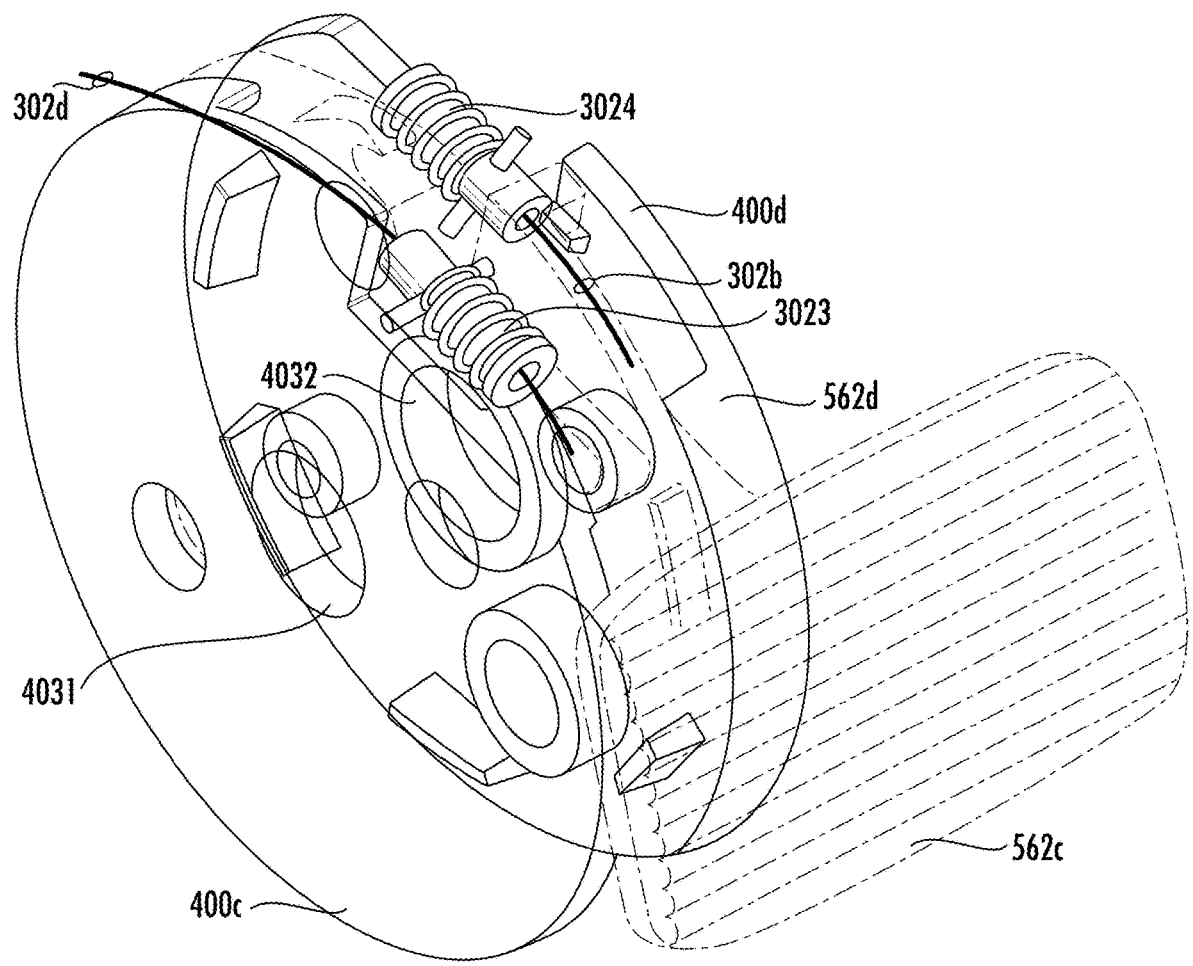
FIG. 8 illustrates steering structures that enable up and down movement of the distal end of the endoscope shaft, in accordance with various embodiments.

In addition to the shaft steering mechanism 56 including, in this embodiment, steering structures that enable left and right movement of the distal end 44 of the endoscope shaft 20, the shaft steering mechanism 56 may also include, according to various embodiments, steering structures that enable up and down movement of the distal end 44 of the endoscope shaft 20. FIG. 8 illustrates additional steering structures that enable up and down movement of the distal end 44 of the endoscope shaft 20. Specifically, FIG. 8 is a partial perspective view (with most of the handle 50 and associated structures hidden so as not to obscure the view of these steering structures) that illustrates an example embodiment of such additional internal steering structures. FIG. 8 shows a third roller wheel 400*c* and a fourth roller wheel 400*d*. The third and fourth roller wheels 400*c*, 400*d* reside within the interior of the handle 50 and between the first and second roller wheels 400*a*, 400*b*. The third roller wheel 400*c* is generally adjacent to the first roller wheel 400*a* (hidden in this view), while the fourth roller wheel 400*d* is generally adjacent to the second roller wheel 400*b* (also hidden in this view). FIG. 8 also shows a thumb knob 562*c*. The thumb knob 562*c* resides outside of the handle 50 and is generally adjacent to the outside surface of the proximal wall of the handle 50 (again, the wall of the handle 50 being hidden in this view).

Each of the third and fourth roller wheels 400*c*, 400*d* define openings 4031, 4032, respectively, at their center. The shaft 401 (shown in FIG. 7*a*) resides within the openings 4031, 4032 of the third and fourth roller wheels 400*c*, 400*d*. As set forth above in connection with FIG. 7*a*, the shaft 401 extends laterally through both side walls of the handle 50 (not shown in this view).

In this embodiment, the third and fourth roller wheels 400*c*, 400*d* are not keyed to the shaft 401 but rather the third and fourth roller wheels 400*c*, 400*d* are able to rotate freely relative to and around the shaft. The thumb knob 562*c* has a connector 562*d* that extends through the proximal wall (not shown) of the handle 50 so as to connect the thumb knob 562*c* to the third and fourth roller sheels 400*c*, 400*d*. In this way, rotation by a user of the thumb knob 562*c* causes the third and fourth roller wheel 400*c*, 400*d* to rotate about the shaft 401.

In the embodiment shown, each of the third and fourth roller wheels 400*c*, 400*d* has a respective steering wire attached thereto. For example, as shown in FIG. 8, the third roller wheel 400*c* is connected to the proximal end of the fourth steering wire 302*d* (only a portion of which is shown in FIG. 8). More specifically, the proximal end of the fourth steering wire 302*d* has a crimp 3023 which fixedly attaches it into a slot on the outer circumference of the third roller wheel 400*c*. In addition, in the embodiment shown, the fourth steering wire 302*d* is wound around the top (in this view) of the third roller wheel 400*c*. Thus, rotation by a user of the thumb knob 562*c* in a downward direction (in this view) causes clockwise rotation (in this view) of the third and fourth roller wheels 400*c*, 400*d*, which in turn causes the proximal end of the fourth steering wire 302*d* to be pulled in the proximal direction. Pulling the proximal end of the fourth steering wire 302d in the proximal direction causes the length of the fourth steering wire 302d to move proximally within the shaft wall and thereby cause the steering collar 309 to move proximally at the circumferential position at which the fourth steering wire 302d is connected. In the embodiment shown, this proximal movement of the fourth steering wire 302d pulls the top of the steering collar 309 such that the distal end 44 of the endoscope shaft 20 is steered upwardly.

As also shown in FIG. 8, the fourth roller wheel 400d is connected to the proximal end of the second steering wire 302b (only a portion of which is shown in FIG. 8). More specifically, the proximal end of the second steering wire 302b has a crimp 3024 which fixedly attaches it into a slot on the outer circumference of the fourth roller wheel 400d. In addition, in the embodiment shown, the second steering wire 302b is wound around the bottom (in this view) of the fourth roller wheel 400d. Thus, rotation by a user of the thumb knob 562c in an upward direction (in this view) causes counter-clockwise rotation (in this view) of the third and fourth roller wheels 400c, 400d, which in turn causes the proximal end of the second steering wire 302b to be pulled in the proximal direction. Pulling the proximal end of the second steering wire 302b in the proximal direction causes the length of the second steering wire 302b to move proximally within the shaft wall and thereby cause the steering collar 309 to move proximally at the circumferential position at which the second steering wire 302b is connected. In the embodiment shown, this proximal movement of the second steering wire 302b pulls the bottom of the steering collar 309 such that the distal end 44 of the endoscope shaft 20 is steered downwardly.

Of course, the above-described arrangement of the steering mechanism 56 is merely one possible such arrangement, and other mechanisms for effectuating the steering of the distal end 44 of the endoscope shaft 20 are also contemplated. For example, steering structures other than, e.g., the above-described roller wheels and roller knobs, may be employed to actuate the left and right movement of the distal end 44 of the endoscope shaft 20. Likewise, steering structures other than, e.g., the above-described roller wheels and thumb knob, may be employed to actuate the up and down movement of the distal end 44 of the endoscope shaft 20. Furthermore, there may be less than or more than the four steering wires illustrated in the embodiment described hereinabove, depending on the number of different directions of movements desired for the distal end 44 of the endoscope shaft 20. Still further, the steering wires may be connected in different circumferential locations around the steering collar 309 such that the steering mechanisms employed in the handle 50 use the steering wires to pull the steering collar 309 in different directions.

As set forth above, in connection with FIG. 1, the distal end 40 of the endoscope shaft 20 may include an illumination source 42, e.g., to provide light at the distal tip 40, and an image capture device 44, e.g., to convey image or video signals related to the region of the distal end 40 of the endoscope shaft 20. FIGS. 11A through 13, which are described below first, illustrate an embodiment having a particular arrangement of an illumination source 42 and an image capture device 44 at the distal end 40 of the endoscope shaft 20. Alternatively, FIGS. 14B, 15 and 16, which are described below thereafter, illustrate another embodiment having a still further arrangement of an illumination source 42 and an image capture device 44 at the distal end 40 of the endoscope shaft 20, providing possible additional benefits, as will be discussed more fully below.

Returning now to FIG. 11A, there is illustrated a front perspective view of a printed circuit board (PCB) 700 that may be employed in the endoscope shaft 20, according an embodiment. More specifically, FIG. 11A illustrates a front perspective view of a circuit board, e.g., a printed circuit board 700, that may be employed at the distal-most end 40 of the endoscope shaft 20 to provide light and generate image signals during a surgical procedure, according an embodiment.

In the embodiment shown, the printed circuit board 700 includes the imaging device 44, in the form of, e.g., a camera sensor 701. It is noted that the imaging device 44 may be any device configured to detect light reflected from the light source 42 and output an image signal. The imaging device 44 can be, for example, a charged coupled device ("CCD") or other suitable imaging sensor. In some embodiments, the imaging device 44 may include at least two lenses providing stereo imaging, or can be an omnidirectional camera.

Figure 11A:
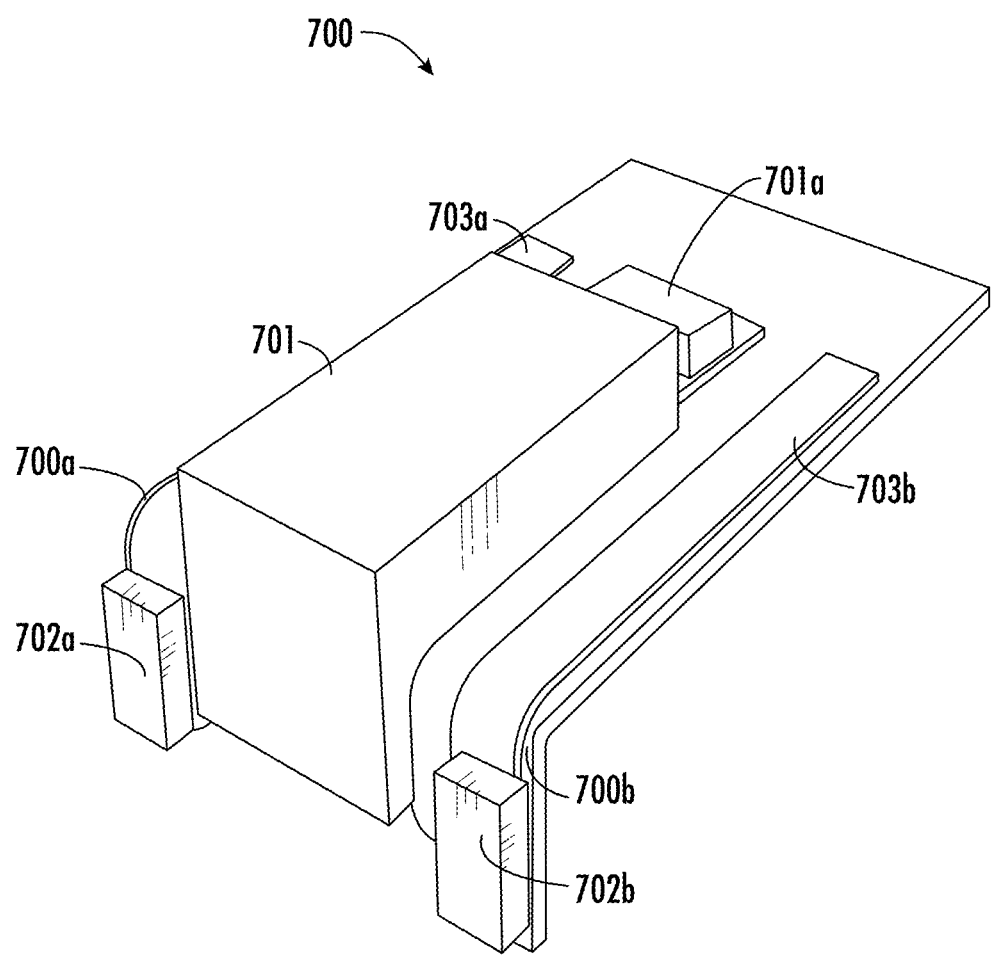
FIG. 11A is a front perspective view that illustrates a printed circuit board (PCB) that may be employed in the endoscope shaft, in accordance with various embodiments.

In the embodiment shown in FIG. 11A, the camera sensor 701 is located in the center of the printed circuit board 700. FIG. 11A also shows that the printed circuit board 700 includes a connection site 701a at which the camera sensor 701 may be connected to a data wire and/or power wire which may be collectively run through a cable, such as an electrical cable 301, that extends longitudinally along the endoscope shaft 20, as will be shown and described in greater detail below in connection with, e.g., FIG. 12.

In the embodiment shown, the printed circuit board 700 also includes the illumination source, e.g., in this case in the form of a pair of LEDs 702a and 702b. Of course, in other embodiments, a single illumination source, e.g., a single LED may be employed. Furthermore, it should be recognized that, in other embodiments, illumination sources other than LEDs, e.g., a halogen bulb, an incandescent bulb, or other suitable light emitter may be employed. Returning to the embodiment shown in FIG. 11A, the pair of LEDs 702a, 702b may be located on opposite sides of the camera sensor 701, so as to be positioned at or near to the opposite lateral edges of the printed circuit board 700. FIG. 11A also shows that the printed circuit board 700 includes connection sites 703a, 703b at which the pair of LEDs 702a, 702b may respectively be connected to one or more power wires, which may be collectively run through a cable, such as the electrical cable 301, that extends longitudinally along the endoscope shaft 20, as will be shown and described in greater detail below in connection with FIG. 12.

Advantageously, the pair of LEDs 702a, 702b may be configured so as to face distally. In this way, the pair of LEDs 702a, 702b may provide increased illumination in a forward-facing direction, thereby primarily illuminating that region within a patient that is located directly in front of the distal end 40 of the endoscope shaft 20. In the embodiment shown, the pair of LEDs 702a, 702b is configured so as to face distally by virtue of distal leg portions 700a, 700b of the printed circuit board 700, and the pair of LEDs 702a, 702b mounted thereon, being bent downwardly, e.g., radially inwardly (in this view) at, e.g., an approximately 90 degree angle so as to be perpendicular, or generally perpendicular, relative to the proximal portion of the printed circuit board 700.

Still further, the printed circuit board 700 may be configured, in accordance with certain embodiments, such that the distal-most face of the pair of LEDs 702a, 702b is flush, e.g., equidistant in a longitudinal direction, with a distal-most face of the camera sensor 701. Having the distal-most face of the pair of LEDs 702a, 702b be flush with a distal-most face of the camera sensor 701 may provide several advantages, e.g., improving the image quality by reducing excessive glare or backlight reflection, additional details of which are set forth in Applicant's co-pending U.S. patent application Ser. No. 18/108,564 filed on Feb. 10, 2023, the entire contents of which are hereby incorporated by reference herein.

Figure 11B:
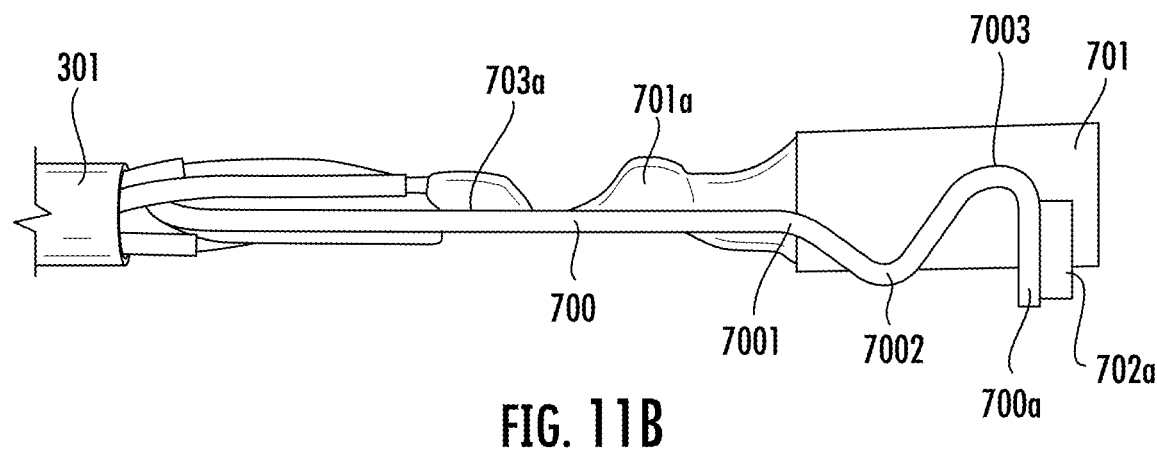
FIG. 11B is a side view of a circuit board that may be employed in the endoscope shaft, in accordance with various embodiments.

As set forth above, FIG. 11A illustrates a front perspective view of a circuit board 700 that may be employed in the endoscope shaft 20 and that includes, according an embodiment, distal leg portions 700a, 700b that are bent downwardly, e.g., radially inwardly (in this view) at, e.g., an approximately 90 degree angle so as to be perpendicular, or generally perpendicular, relative to the proximal portion of the printed circuit board 700. Other configurations for the distal leg portions 700a, 700b may also be employed. For example, FIG. 11B is a side view of a circuit board 700 that may be employed in the endoscope shaft 20 and that includes, according an embodiment, distal leg portions 700a, 700b that include multiple bent regions, e.g., bent regions 7001, 7002, 7003. Collectively, in this embodiment, the multiple bent regions, e.g., bent regions 7001, 7002, 7003 together result in a distalmost portion of each leg 700a, 700b being disposed in a generally perpendicular position relative to the proximal portion of the printed circuit board 700, such that each one of the pair of LEDs 702a, 702b are facing distally.

Figure 11C:
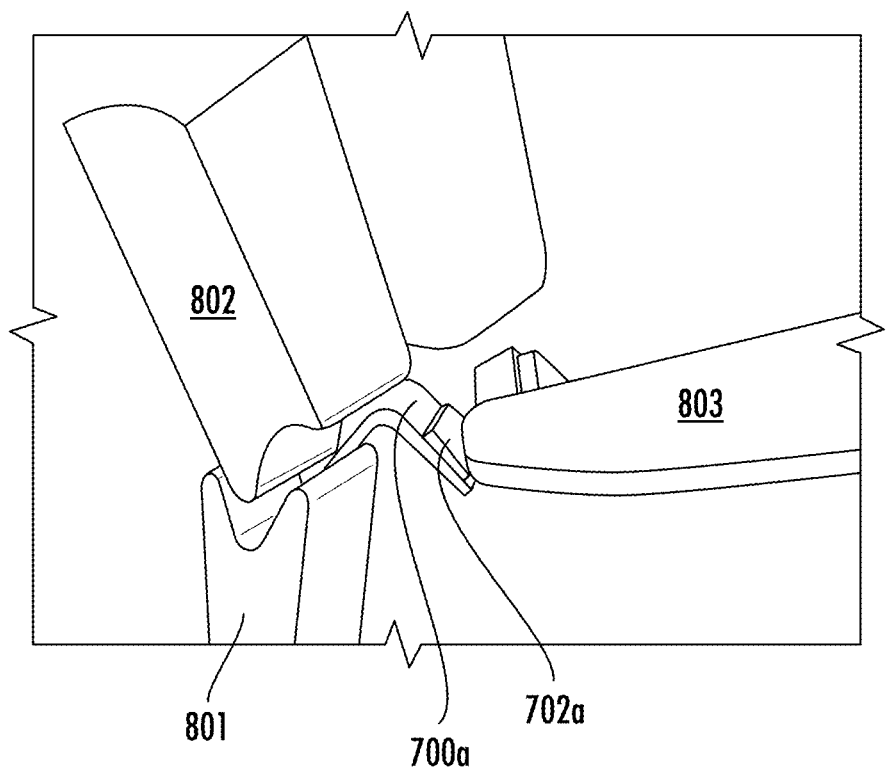
FIG. 11C is a perspective view of a mechanism for forming bends in legs of a circuit board, in accordance with various embodiments.

Of course, any number or degree of bent regions may be employed, according to various embodiments, and these bent regions may be formed by any desired configuration of equipment suitable for doing so. For example, FIG. 11C illustrates a molding process by which several molding dies, e.g., molding dies 801, 802, 803, collectively act on the distal leg portions 700a, 700b so as to bend the distal leg portions 700a, 700b into the shape shown in FIG. 11B.

Figure 12:
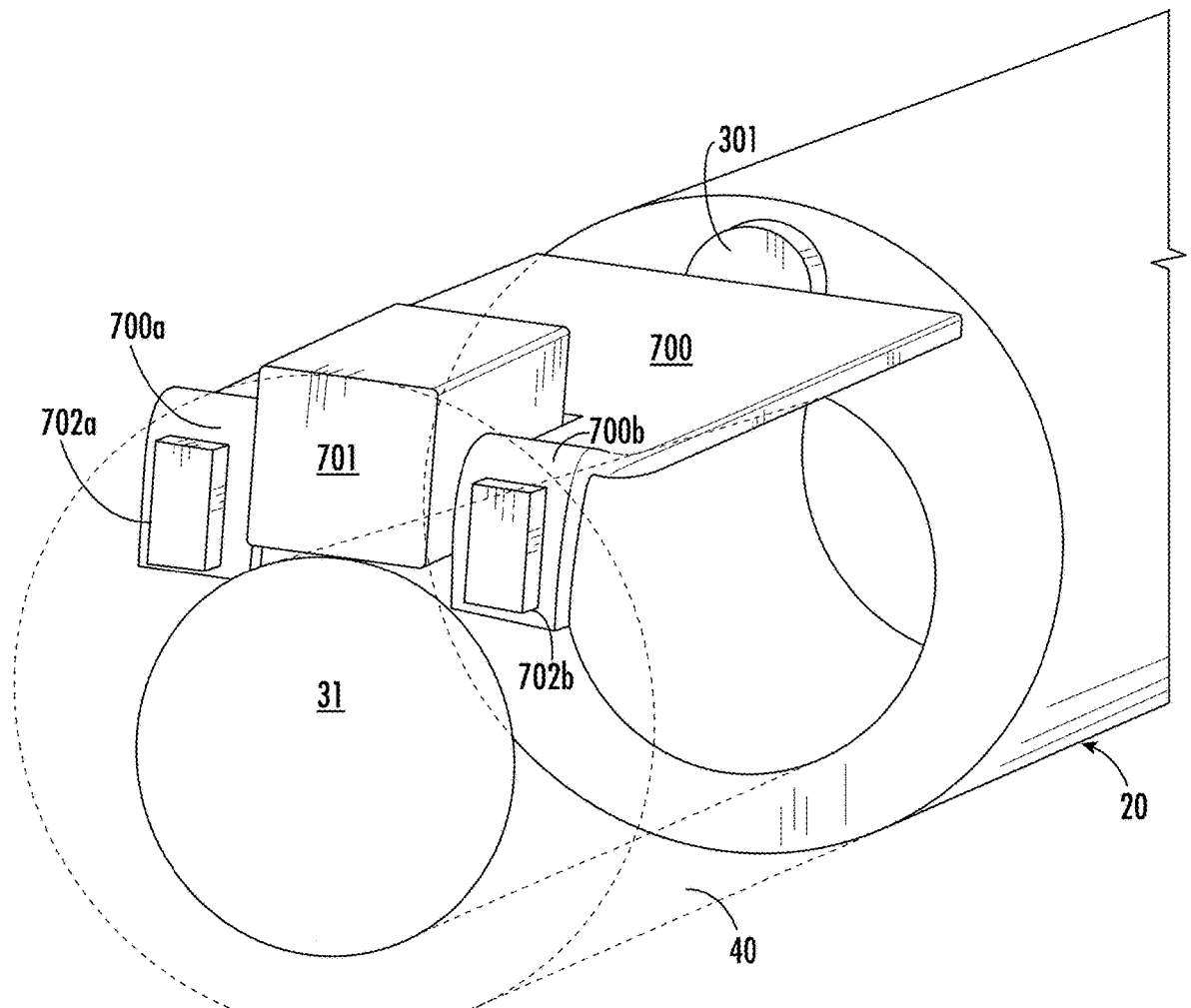
FIG. 12 is a front perspective view of the distal end of the endoscope shaft, in accordance with various embodiments.

FIG. 12 is a front perspective view of the distal end 40 of the endoscope shaft 20, according to an embodiment. In FIG. 12, some components of the endoscope shaft 20 are hidden or shown in phantom so as not to obscure the features shown. In the embodiment shown, the proximal end of the printed circuit board 700 may abut, or otherwise be adjacent to the electrical cable 301 extending longitudinally through the endoscope shaft 20. On the printed circuit board 700, the connection site 701a connects, e.g., by soldering thereto, the camera sensor 701 to a data wire 701b and power wire 701c which collectively run through the electrical cable 301, that extends longitudinally along the endoscope shaft 20. Likewise, on the printed circuit board 700, the connection sites 703a, 703b connect, e.g., by soldering thereto, the respective LEDs 702a, 702b to respective power wires 7021, 7022 which run through the electrical cable 301.

As set forth above, the printed circuit board 700 may be configured, in accordance with certain embodiments, such that the distal-most face of the pair of LEDs 702a, 702b is flush, e.g., equidistant in a longitudinal direction, with a distal-most face of the camera sensor 701. As shown in FIG. 12, in certain embodiments, the distal-most face of the pair of LEDs 702a, 702b and the distal-most face of the camera sensor 701 may be flush relative to each other and to the distal-most face of the endoscope shaft 20. Alternatively, and as shown in FIG. 11B, the distal-most face of the pair of LEDs 702a, 702b may be recessed relative to a distal-most face of the camera sensor 701 and/or to the distal-most face of the endoscope shaft 20. In addition to the advantages set forth above (e.g., less glare and/or backlight reflection, etc), having the distal-most face of the pair of LEDs 702a, 702b and the distal-most face of the camera sensor 701 also be flush and/or recessed relative to the distal-most face of the endoscope shaft 20 may have still further advantages. For example, having the distal-most face of the pair of LEDs 702a, 702b and the distal-most face of the camera sensor 701 also be flush and/or recessed relative to the distal-most face of the endoscope shaft 20 may simplify manufacturing, in that a protuberance-free surface is provided at the distal-most face of the endoscope shaft 20 for any protective layer, e.g., coating or laminate etc., that may be applied to such distal-most face of the endoscope shaft 20. Furthermore, having the distal-most face of the pair of LEDs 702a, 702b and the distal-most face of the camera sensor 701 also be flush and/or recessed relative to the distal-most face of the endoscope shaft 20 may simplify operation, in that a protuberance-free surface being provided at the distal-most face of the endoscope shaft 20 may help reduce the possibility that an instrument that is passed through the working channel of the endoscope shaft 20 is snagged on or otherwise undesirably contacts either of the pair of LEDs 702a, 702b or the camera sensor 701. Still further, having the distal-most face of the pair of LEDs 702a, 702b and the distal-most face of the camera sensor 701 also be flush relative to the distal-most face of the endoscope shaft 20 may help improve safety, in that a protuberance-free surface being provided at the distal-most face of the endoscope shaft 20 may help reduce the possibility that the distal-most face of the endoscope shaft 20 irritates or otherwise injures the sensitive tissue within a patient as the endoscope shaft 20 is introduced and inserted through the patient's nasal cavity, sinus cavity, esophagus, etc.

In this embodiment, the printed circuit board 700 is mounted within the shaft wall of the endoscope shaft 20. In the view shown, the printed circuit board 700 is positioned entirely within the shaft wall, e.g., such that all portions of the printed circuit board 700 are positioned laterally outside of the inner diameter of the working channel 31, while all portions of the printed circuit board 700 are positioned laterally within the outer diameter of the endoscope shaft 20. Having all portions of the printed circuit board 700 be positioned laterally outside of the inner diameter of the working channel 31, while also being positioned laterally within the outer diameter of the endoscope shaft 20, may provide several advantages. For example, having all portions of the printed circuit board 700 be positioned laterally outside of the inner diameter of the working channel 31, while also being positioned laterally within the outer diameter of the endoscope shaft 20, enables the working channel 31 to be completely clear of any obstructions. Enabling the working channel 31 to be completely clear of any obstructions may simplify manufacturing, e.g., in that any material that forms the endoscope shaft 20 or any protective layer or coating thereof may avoid the working channel 31. Furthermore, enabling the working channel 31 to be completely clear of any obstructions may simplify operation, in that an obstruction-free working channel 31 may help reduce the possibility that an instrument that is passed through the working channel 31 of the endoscope shaft 20 is snagged on or otherwise interferes with the function of, e.g., damaging or blocking the view of, the pair of LEDs 702a, 702b or the camera sensor 701 while within the working channel 31. Still further, enabling the working channel 31 to be completely clear of any obstructions may help improve safety, in that an obstruction-free working channel 31 may help reduce the possibility that an instrument inserted through the working channel 31 is damaged or otherwise impeded in its movement, which could negatively impact the surgical procedure, e.g., it could cause a biopsy sample to be harmed or dropped, it could cause broken components to be left behind in the surgical site, etc.

The configuration of the printed circuit board 700, and of the camera sensor 701 and the pair of LEDs 702*a*, 702*b* mounted thereon, as shown in FIG. 12, may also provide the advantage that the shaft wall of the endoscope shaft 20 may have the smallest thickness possible. Having the smallest wall thickness possible for the endoscope shaft 20 may help enable the endoscope shaft 20 to maximize the inner diameter of the working channel, e.g., so as to enable the largest range of instruments to be passed therethrough, while minimizing the outer diameter of the endoscope shaft 20, e.g., so as to cause as little discomfort to the patient as possible when the endoscope shaft 20 is inserted into the patient. This, in turn, may help to optimize the endoscope shaft for procedures such as, e.g., pediatric trans-nasal endoscopy procedures, for which these characteristics of the endoscope shaft 20 are particularly important.

As mentioned above, in the embodiment shown in FIG. 12, the pair of LEDs 702*a*, 702*b* is configured so as to face distally by virtue of distal leg portions 700*a*, 700*b* of the printed circuit board 700, and the pair of LEDs 702*a*, 702*b* mounted thereon, being bent downwardly, e.g., radially inwardly (in this view) at a 90 degree angle so as to be perpendicular relative to the proximal portion of the printed circuit board 700. Because the working channel 31 is round and its outer diameter thereby has a curvature, the distal legs 700*a*, 700*b* of the printed circuit board 700 are, in the embodiment shown, advantageously bent into a position such that the bottom-most edge of the LEDs 702*a*, 702*b* are positioned lower than (in this view) the bottom-most edge of the camera sensor 701. This positions the pair of LEDs 702*a*, 702*b* closer to the center of the working channel 31 than the pair of LEDs 702*a*, 702*b* would otherwise be were the distal legs 700*a*, 700*b* of the printed circuit board 700 instead bent into a position at which the bottom-most edge of the LEDs 702*a*, 702*b* were even with the bottom-most edge of the camera sensor 701. Thus, having the distal legs 700*a*, 700*b* of the printed circuit board 700 bent into a position such that the bottom-most edge of the LEDs 702*a*, 702*b* are positioned lower than the bottom-most edge of the camera sensor 701 helps to enable the wall thickness of the endoscope shaft 20 to be minimized, since this configuration follows the curvature of the working channel 31 and the outer diameter of the endoscope shaft 20. Still further, having the distal legs 700*a*, 700*b* of the printed circuit board 700 bent into a position such that the bottom-most edge of the LEDs 702*a*, 702*b* are positioned lower than the bottom-most edge of the camera sensor 701 positions the LEDs 702*a*, 702*b* closer to any tissue that is positioned directly in front of the working channel 31, thereby ensuring that such tissue is optimally lit by the pair of LEDs 702*a*, 702*b* during a surgical procedure.

Figure 13:
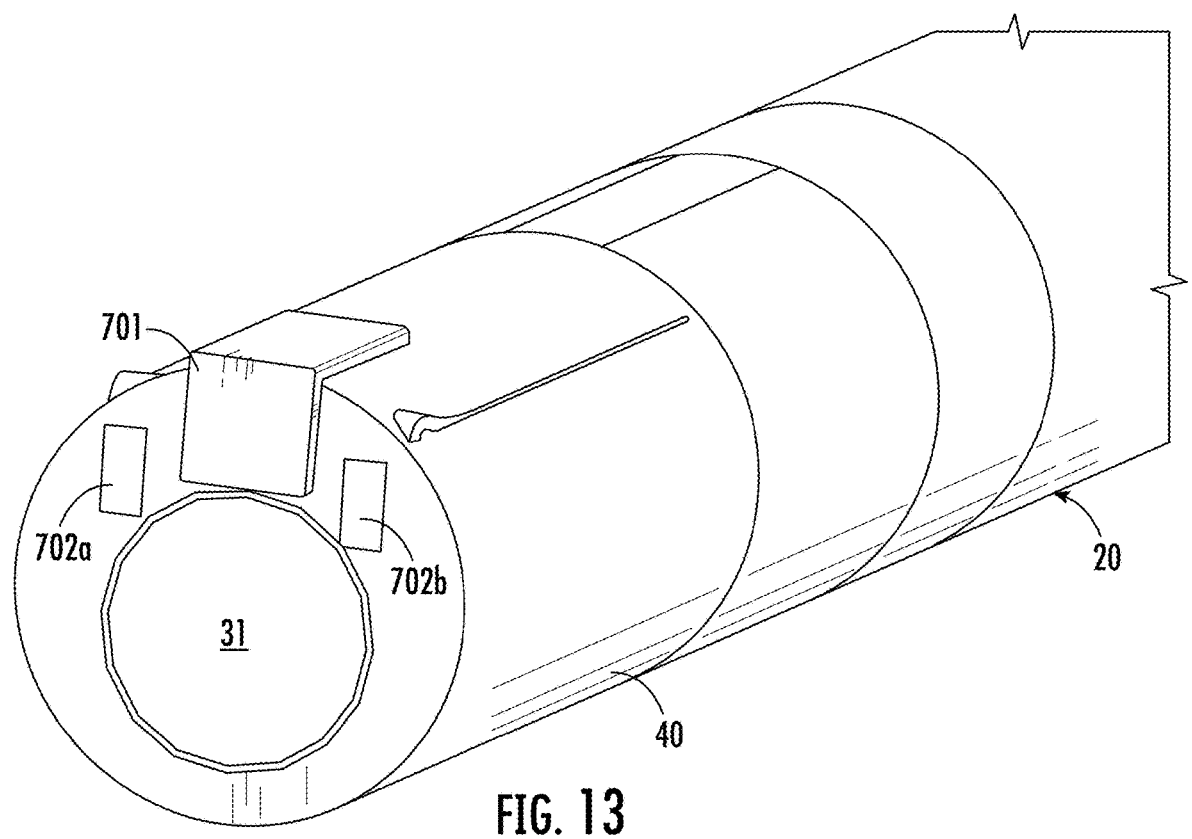
FIG. 13 is a front perspective view similar to that shown in FIG. 12, but having the distal region of the endoscope shaft enclosed by a protective layer, in accordance with various embodiments.

FIG. 13 is a front perspective view similar to that shown in FIG. 12, but having the distal region 40 of the endoscope shaft 20 enclosed by a protective layer such as a micro-molded tip component, as is described further hereinbelow. In various embodiments, the printed circuit board 700 may be mounted to the distal region 40 of the endoscope 20 via one or more of a pattern of braided filaments, e.g., the filaments being alternatingly woven over and under the printed circuit board 70 and around the working channel 31 so as to fix the printed circuit board 700 in position at the distal end of the endoscope 20. Additionally or alternatively, the printed circuit board 700 may be mounted to the distal region 40 of the endoscope 20, via a laminate layer of flexible polymer, such as Pebax® 35 (Pebax® being a tradename for a thermoplastic elastomer of polyether block amide, obtained by, e.g. polycondensation of a carboxylic acid polyamide with an alcohol termination polyether, available commercially from, e.g., Compounding Solutions in Lewiston, ME) or other suitable material. Various possible configurations for the endoscope shaft 20 being formed of a braided pattern of woven filaments and/or having protective laminate layers of flexible polymer are shown and described in additional detail in the above-referenced Applicant's co-pending patent applications, and as further described hereinbelow. As shown in FIG. 13, neither the pair of LEDs 702*a*, 702*b* nor the camera sensor 701 impedes the distal opening into the working channel 31, thereby ensuring an obstruction-free passage of instruments therethrough.

As mentioned above, in embodiments, the distalmost tip of the endoscope shaft 20 may be comprised of a micro-molded Pebax® 55D tip component that has an opening sized to accept the camera sensor 701. Such a micro-molded tip component may also include translucent pockets to the sides of the opening that situate the LEDs 702*a*, 702*b* adjacent to the camera sensor 701. Having the camera sensor 701 exposed through an opening in such a micro-molded tip component may, according to embodiments and as previously mentioned above, provide an arrangement in which material is not disposed in front of, e.g., distally relative to, the camera sensor 701, thereby preventing or reducing light filtration or distortion. In such an embodiment having pockets therein, the LEDs 702*a*, 702*b* may be maintained essentially flush with, or in some embodiments slightly proximal to (as shown in FIG. 11B), a face of the camera sensor 701 to prevent light from, e.g., bleeding, into the camera sensor 701. Still further, the distalmost edges of such a micro-molded tip may be contoured, or otherwise curved, such that the distalmost edges present an atraumatic surface to the patient during insertion and manipulation. As shown and mentioned above in connection with FIG. 12, the proximal end of the printed circuit board 700 may abut, or otherwise be adjacent to, a distal end of the electrical cable 301 extending longitudinally through the endoscope shaft 20 such that the pair of LEDs 702*a*, 702*b* and the camera sensor 701 may each be connected to, e.g., by soldering wires that extend to the distal end of the electrical cable 301.

Figure 14A:
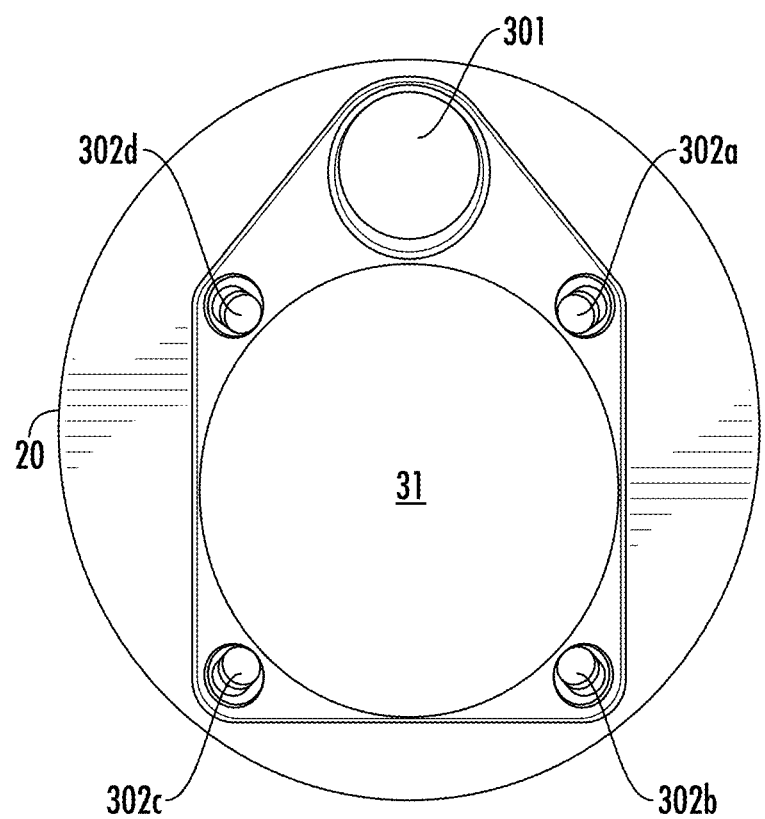
FIG. 14A is a front cross-sectional view of a shaft 20 having the steering wires positioned in the 45, 135, 225 and 315 degree positions, respectively, around the working channel, in accordance with various embodiments.

As set forth above, in various embodiments (such as shown in, e.g., FIG. 4), the four steering wires 302*a*, 302*b*, 302*c*, 302*d* may be also disposed within the wall of the endoscope shaft 20 so as to each be positioned 90 degrees apart relative to each other, with the steering wires 302*a* and 302*d* each being spaced 45 degrees apart from the camera electrical cable 301 that is located at the top-most circumferential position of the endoscope shaft 20. In such an arrangement, the first steering wire 302*a* may be located within the shaft 20 at, e.g., a 45 degree clockwise position relative to the top-most position along the outer circumference of the working channel 31, the second steering wire 302*b* is located at, e.g., a 135 degree clockwise position, the third steering wire 302*c* may be located at, e.g., a 225 degree clockwise position, and the fourth steering wire 302*d* may be located at, e.g., a 315 degree clockwise position, and each of the four steering wires 302*a*, 302*b*, 302*c*, 302*d* maintain their respective circumferential positions relative to the working channel 31 along the full length of the endoscope shaft 20 so as to also be in the 45, 135, 225 and 315 degree positions, respectively, relative to the working channel 31 at the distal end 40 of the endoscope shaft 20, where they connect to a steering collar (as shown and described in connection with FIG. 6). Such an arrangement is shown, for example, in FIG. 14A, which illustrates a front cross-sectional view of the shaft 20.

In alternative embodiments, however, the four steering wires 302a, 302b, 302c, 302d may instead be circumferentially arranged within the shaft 20, and/or may be circumferentially attached to the steering collar 309, at different circumferential positions, e.g., at the 0, 90, 180 and 270 degree clockwise position relative to the top-most position of the working channel 31. Such an arrangement is shown and described in connection with FIG. 14B, which is a front cross-sectional view of the shaft 20 having the steering wires 302a, 302b, 302c, 302d positioned in the 0, 90, 180 and 270 degree positions, respectively, around the working channel 31. Having the four steering wires 302a, 302b, 302c, 302d be circumferentially arranged within the shaft 20, and/or may be circumferentially attached to the steering collar 309, at the 0, 90, 180 and 270 degree clockwise position relative to the top-most position of the working channel 31 may provide certain advantages as compared to other positions. For example, when a user operates the roller knobs 562a, 562b and/or the thumb knob 562c on the handle 50 so as to steer the distal tip of the shaft 20, having the four steering wires 302a, 302b, 302c, 302d be circumferentially arranged within the shaft 20, and/or circumferentially attached to the steering collar 309, at the 0, 90, 180 and 270 degree clockwise position relative to the top-most position of the working channel 31 may help ensure that the distal tip of the shaft 20 actually moves in the true right-or-left and/or true up-and-down directions, since the steering wires are actually attached at these locations. This may enable a user to be more accurate with his or her steering, since the movement of the roller knobs 562a, 562b and thumb knob 562c are more closely aligned with directions that the distal tip of the shaft 20 will move.

Figure 14B:
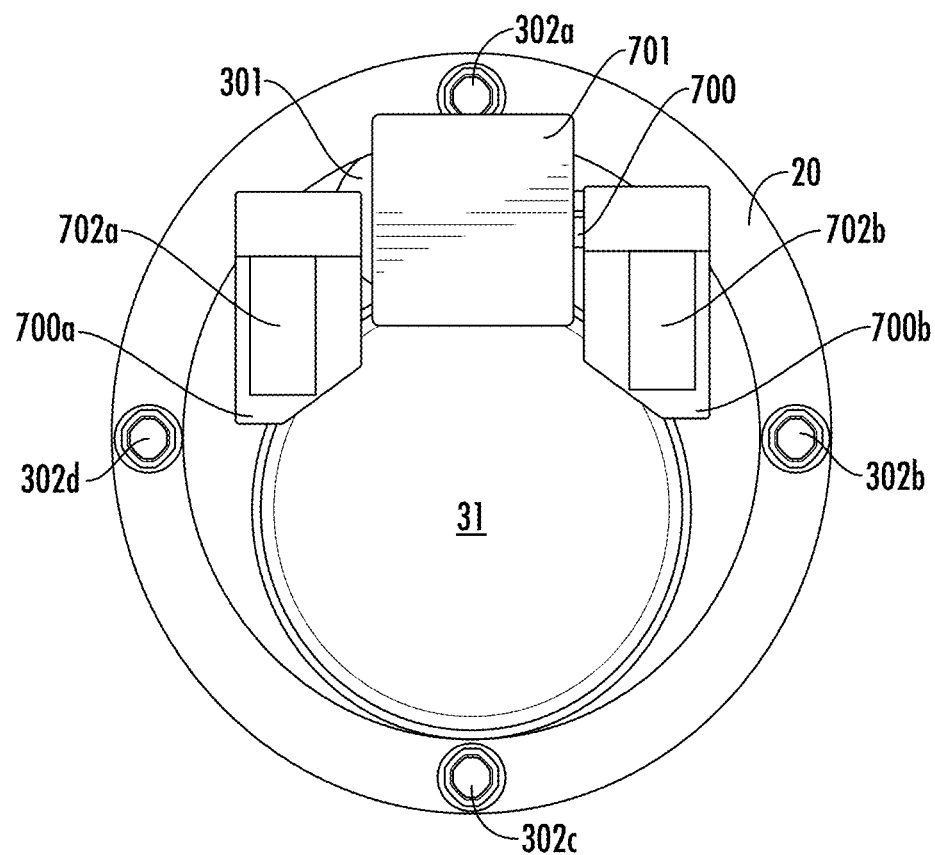
FIG. 14B is a front cross-sectional view of a shaft 20 having the steering wires positioned in the 0, 90, 180 and 270 degree positions, respectively, around the working channel, in accordance with various embodiments.

Referring to FIG. 14B, there is illustrated the imaging device 44, in the form of, e.g., a camera sensor 701, which may be mounted on a printed circuit board 700 (partially hidden in this view), such as the printed circuit board 700 illustrated in FIG. 11A. As mentioned above, the imaging device 44 may be any device configured to detect light reflected from the light source 42 and output an image signal. The imaging device 44 can be, for example, a charged coupled device ("CCD") or other suitable imaging sensor. In some embodiments, the imaging device 44 may include at least two lenses providing stereo imaging, or can be an omnidirectional camera.

In the embodiment shown in FIG. 14B, the camera sensor 701 is located in the center of the printed circuit board 700. Although not shown in FIG. 14B, the printed circuit board 700 may include a connection site (such as the connection site 701a as shown in FIG. 11A) at which the camera sensor 701 may be connected to a data wire and/or power wire which may be collectively run through a cable, such as an electrical cable 301, that extends longitudinally along the endoscope shaft 20, as will be shown and described in greater detail below in connection with, e.g., FIG. 15.

In the embodiment shown in FIG. 14B, the printed circuit board 700 also includes the illumination source, e.g., in this case in the form of a pair of LEDs 702a and 702b. Of course, in other embodiments, a single illumination source, e.g., a single LED may be employed. Furthermore, it should be recognized that, in other embodiments, illumination sources other than LEDs, e.g., a halogen bulb, an incandescent bulb, or other suitable light emitter may be employed. Returning to the embodiment shown in FIG. 14B, the pair of LEDs 702a, 702b are located on opposite sides of the camera sensor 701, so as to be positioned at or near to the opposite lateral edges of the printed circuit board 700. Although partially hidden from view in FIG. 14B, the printed circuit board 700 may also include connection sites (such as the connection sites 703a, 703b shown in FIG. 11A) at which the pair of LEDs 702a, 702b may respectively be connected to one or more power wires, which may be collectively run through a cable, such as the electrical cable 301, that extends longitudinally along the endoscope shaft 20.

Advantageously, and as mentioned above, the pair of LEDs 702a, 702b may be configured so as to face distally so as to provide increased illumination in a forward-facing direction, thereby primarily illuminating that region within a patient that is located directly in front of the distal end 40 of the endoscope shaft 20. In the embodiment shown, and similar to that shown in FIG. 11A, the pair of LEDs 702a, 702b in FIG. 14B is configured so as to face distally by virtue of distal leg portions 700a, 700b of the printed circuit board 700, and the pair of LEDs 702a, 702b mounted thereon, being bent downwardly, e.g., radially inwardly (in this view) at, e.g., an approximately 90 degree angle so as to be perpendicular, or generally perpendicular, relative to the proximal portion of the printed circuit board 700. Of course, any number or degree of bent regions may be employed, according to various embodiments, and these bent regions may be formed by any desired configuration of equipment suitable for doing so. Still further, and for the reasons set forth above, the printed circuit board 700 may be configured, in accordance with certain embodiments, such that the distal-most face of the pair of LEDs 702a, 702b may be flush, e.g., equidistant in a longitudinal direction, with a distal-most face of the camera sensor 701.

Figure 15:
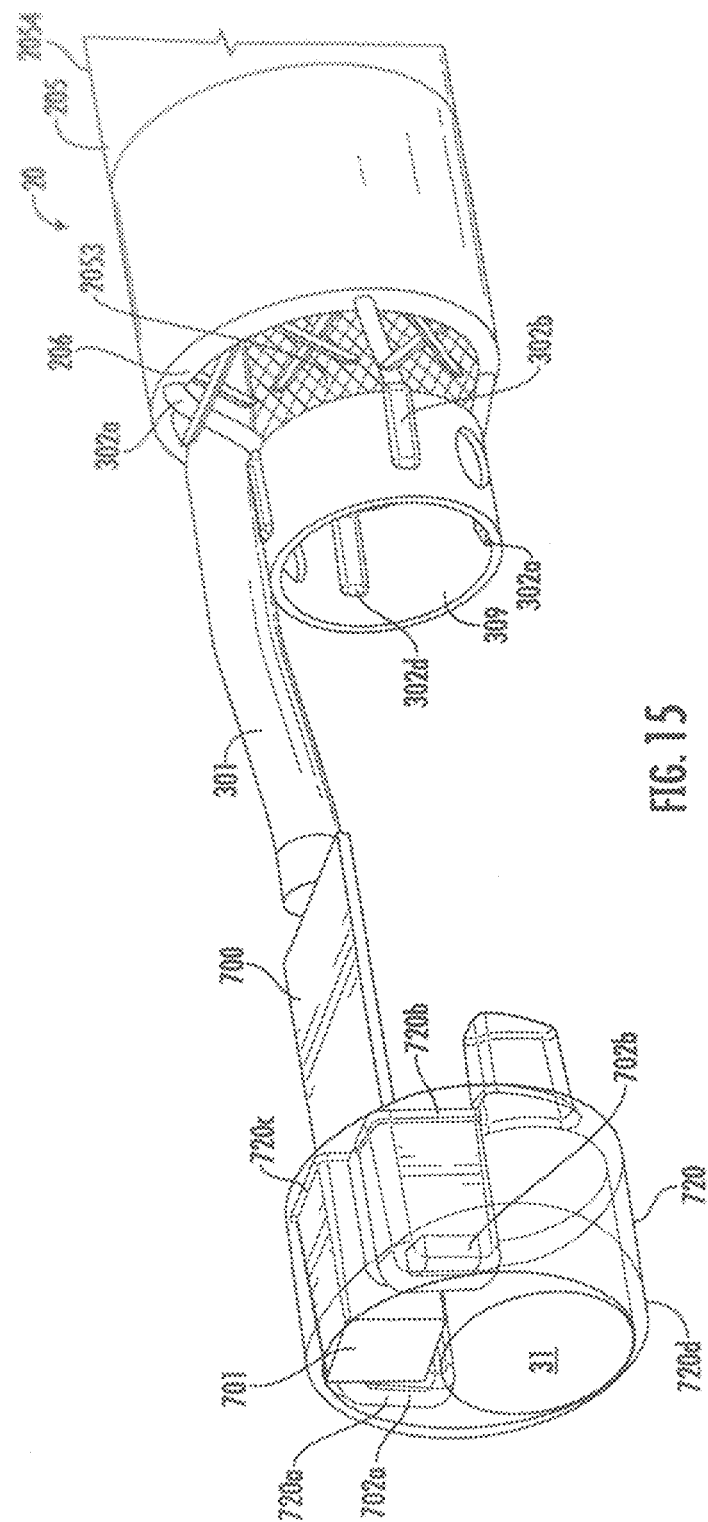
FIG. 15 is a side perspective view of the shaft shown in FIG. 11A, in accordance with various embodiments.

While FIG. 11A is a front cross-sectional view, FIG. 15 is a side perspective view of the shaft 20 shown in FIG. 11A. In the view of FIG. 15, some portions of the shaft 20 etc, are hidden or shown in phantom so as to illustrate additional features of the shaft 20. In the embodiment shown, the proximal end of the printed circuit board 700 may abut, or otherwise be adjacent to the electrical cable 301 extending longitudinally through the endoscope shaft 20. The printed circuit board 700 connects the camera sensor 701 to a data wire (not shown in this view, but may be similar to data wire 701b) and a power wire (also not shown in this view, but may also be similar to power wire 701c) which collectively run through the electrical cable 301. In an embodiment, the camera sensor 701 may be connected to the electrical cable 301 by, e.g., soldering the respective wires and connection points. However, in other embodiments, the camera sensor 701 may be connected to the electrical cable 301 without soldering, thereby simplifying and expediting the manufacturing process thereof. Likewise, on the printed circuit board 700, connection sites (such as the connection sites 703a, 703b) may connect, e.g., either with or without soldering thereto, the respective LEDs 702a, 702b to respective power wires 7021, 7022 which run through the electrical cable 301.

As mentioned above and as illustrated in FIG. 15, the printed circuit board 700—along with the pair of LEDs 702a, 702b and the camera sensor 701 mounted thereon—may be mounted at the distal tip of the shaft 20 via a micro-molded tip component 720 that has an opening 720c sized to accept the camera sensor 701. Such a micro-molded tip component 720 may also include translucent pockets 720b, 720c to the sides of the opening 720c that house the LEDs 702a, 702b adjacent to the camera sensor 701. Having the camera sensor 701 exposed through an opening in such a micro-molded tip component may, according to embodiments and as previously mentioned above, provide an arrangement in which material is not disposed in front of, e.g., distally relative to, the camera sensor 701, thereby preventing or reducing light filtration or distortion. In such an embodiment having pockets therein, the LEDs 702a, 702b may be maintained essentially flush with, or in some embodiments slightly proximal to (as shown in FIG. 15) a face of the camera sensor 701 to prevent light from, e.g., bleeding, into the camera sensor 701. Still further, the distalmost edges 720d of such a micro-molded tip component 720 may be contoured, or otherwise curved, such that the distalmost edges 720d present an atraumatic surface to the patient during insertion and manipulation. As shown and mentioned above in connection with FIG. 12, the proximal end of the printed circuit board 700 may abut, or otherwise be adjacent to, a distal end of the electrical cable 301 extending longitudinally through the endoscope shaft 20 such that the pair of LEDs 702a, 702b and the camera sensor 701 may each be connected to by wires that extend to the distal end of the electrical cable 301.

As also shown in FIG. 15, the electrical cable 301 and the steering wires 302a, 302b, 302c, 302d run longitudinally within the wall of the shaft 20. In a specific embodiment, and as shown in FIG. 15, the steering wires 302a, 302b, 302c, 302d run longitudinally within, e.g., inside of, the wall of an outer jacket 205 of the shaft 20. In addition, in this specific embodiment and as shown in FIG. 15, the electrical wire 301 runs longitudinally in an open space between the outer jacket 205 and an inner channel or inner sheath 206 of the shaft 20, the inner channel or sheath 206 ("channel 206" hereafter for simplicity sake only) of the shaft defining the working channel 31 of the shaft 20. The outer jacket 205 may be formed from a single layer of material, or, as best shown in FIG. 15, the outer jacket 205 may include an outermost layer 2054 that covers an inner layer 2053. In embodiments, the inner layer 2053 of the outer jacket may be formed via braiding (as described more fully above). In addition, in embodiments, the outermost layer 2054 of the outer jacket may be formed from a different, e.g., non-braided, material that is more lubricious than the inner layer 2053 so as to more smoothly and easily travel into a patient's sensitive tissue passages, and/or so as to protect the braided fibers of the inner layer from fraying or otherwise being damaged or causing damage.

Figure 16:
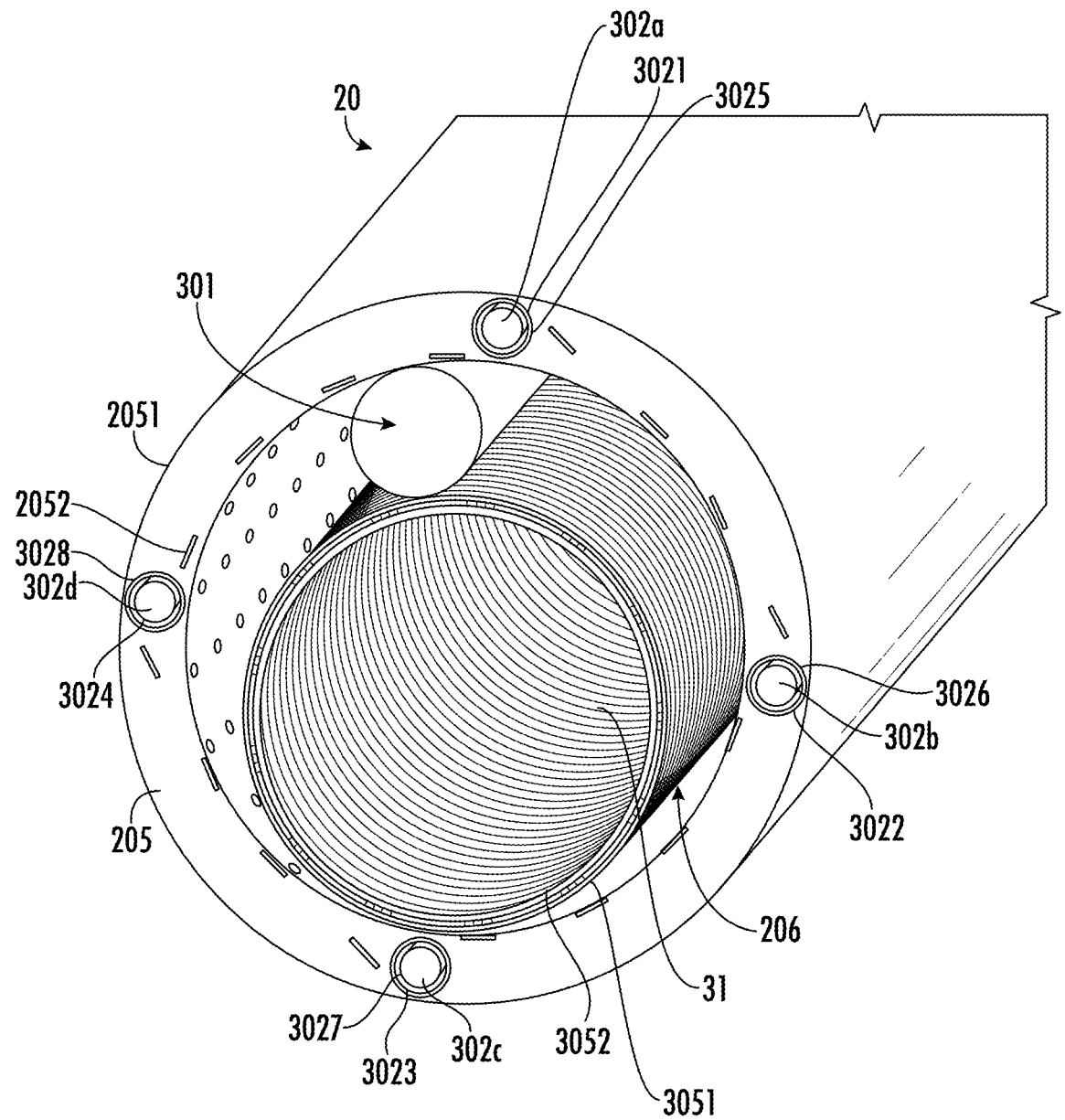
FIG. 16 is a front perspective cross-sectional view illustrating certain features of a shaft at a location proximal to the steering collar, in accordance with various embodiments.

Additional details of such an embodiment are shown and described in connection with FIG. 16. FIG. 16 is a front perspective cross-sectional view of the shaft 20 illustrating these features of the shaft 20 at a location proximal to the steering collar 309. For example, and as shown in FIG. 16, the steering wires 302a, 302b, 302c, 302d run longitudinally within, e.g., inside of, the wall of an outer jacket 205 of the shaft 20. More specifically, the steering wires 302a, 302b, 302c, 302d run longitudinally between an outer surface 2051 and the inner surface 2052 of the outer jacket 205. Advantageously, the outer jacket 205 has lumen 3021, 3022, 3023, 3024 that are fixed within, e.g., by being molded or otherwise formed, into the outer jacket 205 such that the lumen 3021, 3022, 3023, 3024 extend longitudinally between the outer surface 2051 and the inner surface 2052, with the steering wires 302a, 302b, 302c, 302d extending longitudinally within and through respective ones of the lumen 3021, 3022, 3023, 3024.

In embodiments, the lumen 3021, 3022, 3023, 3024 may be formed by the material of the outer jacket 205 itself, such that the steering wires 302a, 302b, 302c, 302d extend longitudinally within and through respective ones of lumen 3021, 3022, 3023, 3024 formed by the material of the outer jacket 205. Alternatively, the lumen 3021, 3022, 3023, 3024 may be formed not by the material of the outer jacket 205 itself but rather by tubular sheaths 3025, 3026, 3027, 3028 that are fixed within, e.g., by being molded and/or braided, into the outer jacket 205, the tubular sheaths 3025, 3026, 3027, 3028 defining a respective one of the lumen 3021, 3022, 3023, 3024 therethrough. In this arrangement, the steering wires 302a, 302b, 302c, 302d extend longitudinally within and through respective ones of lumen 3021, 3022, 3023, 3024 formed by respective ones of the tubular sheaths 3025, 3026, 3027, 3028. In this way, the tubular sheaths 3025, 3026, 3027, 3028 may be made from a different material, e.g., a material that is more durable and/or more lubricious, than the material from which the outer jacket 205 is made. Thus, in an embodiment in which the tubular sheaths 3025, 3026, 3027, 3028 are made from a material that is more lubricious than the material from which the outer jacket 205 is made, the steering wires 302a, 302b, 302c, 302d may be moved longitudinally within and through their respective lumen 3021, 3022, 3023, 3024 formed by their respective tubular sheaths 3025, 3026, 3027, 3028 with less friction than would otherwise be experienced if the steering wires 302a, 302b, 302c, 302d extended through respective ones of lumen 3021, 3022, 3023, 3024 formed by the material of the outer jacket 205 itself. Likewise, in an embodiment in which the tubular sheaths 3025, 3026, 3027, 3028 are made from a material that is more durable than the material from which the outer jacket 205 is made, the steering wires 302a, 302b, 302c, 302d may be moved longitudinally within and through their respective lumen 3021, 3022, 3023, 3024 formed by their respective tubular sheaths 3025, 3026, 3027, 3028 with less likelihood that the outer jacket 205 would be damaged or punctured by the movement of the steering wires 302a, 302b, 302c, 302d therewithin and therethrough.

In embodiments, and as previously mentioned, the outer jacket 205 of the shaft 20 may be formed as a molded component, it may be formed by braiding fibers along some or a portion of it length, and/or may be formed by any combination thereof, such as the combination of the outer protective outer layer 2054 and a braided inner layer 2053 as shown in FIG. 15. Likewise, any or all of the steering wires 302a, 302b, 302c, 302d, their respective lumen 3021, 3022, 3023, 3024, and their respective tubular sheaths 3025, 3026, 3027, 3028 may be formed or situated in any of these layers of the outer jacket 205.

FIG. 16 also illustrates, in this embodiment, that the electrical wire 301 runs longitudinally in an open space between the outer jacket 205 and an inner channel wall 206 of the shaft 20. More specifically, FIG. 16 illustrates, in this embodiment, that the inner channel 206 of the shaft may include an outer surface 3051 and an inner surface 3052. The inner surface 3052 of the inner channel 206 may define the working channel 31 of the shaft 20, through which instruments and/or air, gas or water/suction may flow, as described more fully above. In this embodiment, the electrical wire 301 runs longitudinally in the open space between the inner surface 2052 of the outer jacket 205 and the outer surface 3051 of the inner channel 206. In the embodiment shown, the electrical wire 301 runs generally parallel to, and slightly off of, the 0 degree topmost position of the shaft 20. In this way, and as best shown in FIG. 15, the electrical wire 301 does not interfere with the steering wire 302a which itself resides at that 0 degree topmost position of the shaft 20.

Having the electrical wire 301 run longitudinally in the open space between the outer jacket 205 and the inner channel wall 206 of the shaft 20 may provide additional advantages. For example, and as mentioned previously, the endoscope shaft 20 may benefit from having greater flexibility along its longitudinal length for improved bending and steering capabilities, particularly with respect to patient comfort. While embodiments described above include a shaft 20 that has varying amounts of flexibility at different portions of its longitudinal length in order to provide patient comfort zones therealong, an embodiment such as shown in, e.g., FIGS. 16, in which the electrical wire 301 runs longitudinally in the open space between the outer jacket 205 and the inner channel wall 206 of the shaft 20, may provide for improved flexibility of the shaft 20 over its entire length, e.g., thereby providing a patient comfort zone along the entire length of the shaft 20. This flexibility of the shaft 20 over its entire length may be achieved, at least in part, because the open space between the outer jacket 205 and the inner channel wall 206 of the shaft 20 may reduce friction between the outer jacket 205 and the inner channel wall 206 as they are bent, and/or may provide additional internal space within the shaft 20 for the bending to occur. Of course, it should be recognized that the improved flexibility of the shaft 20 may be provided, not merely by the existence of the open space between the outer jacket 205 and the inner channel wall 206, but also by other factors, e.g, the dimensions, flexibility and braid count of the other portions of the shaft 20.

Figure 17:
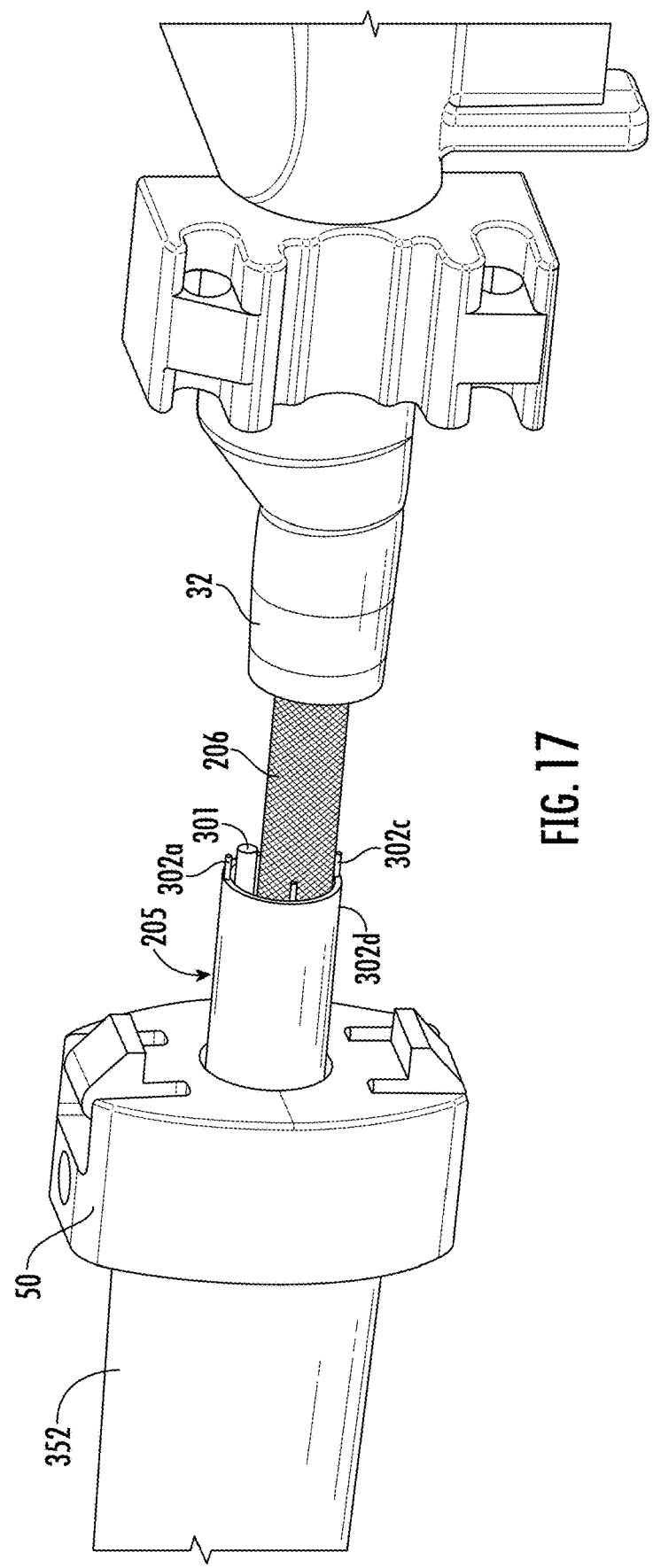
FIG. 17 is a side perspective view of a handle, with the outer shell of the handle removed, and illustrating the shaft configuration within the interior of the handle, in accordance with various embodiments.
Figure 18:
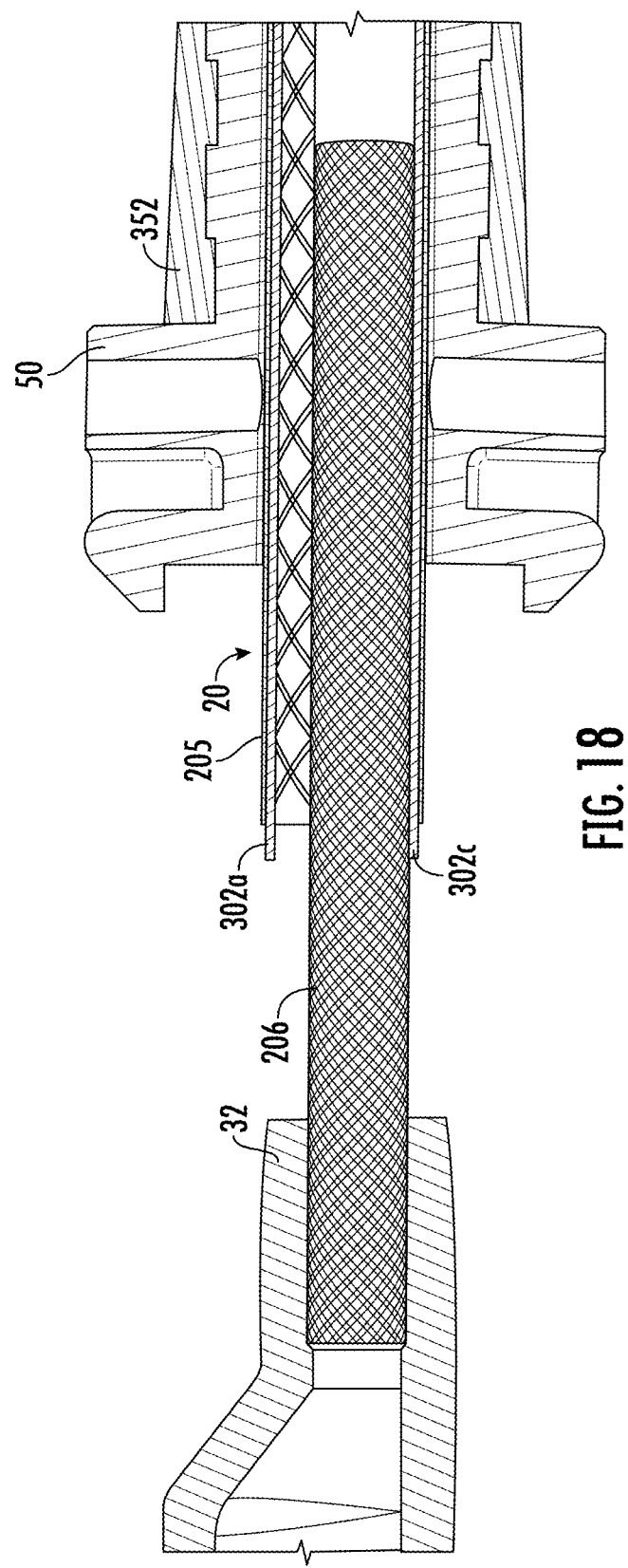
FIG. 18 is a side cross-sectional view of the handle shown in FIG. 17, in accordance with various embodiments.

FIGS. 17 and 18 provide additional details of the shaft 20 as the shaft 20 enters into the handle 50. Specifically, FIG. 17 is a side perspective view of the handle 50, with the outer shell of the handle 50 removed so as to illustrate the interior thereof, while FIG. 18 is a side cross-sectional view of the handle 50. In the embodiment shown, the shaft 20 extends distally from a distal portion of the handle 50 (protected by a reinforcing component 352 which prevents over-bending of the shaft 20 relative to the handle, as shown and described more fully in applicant's co-pending U.S. Patent Application Ser. No. 63/499,686 filed May 2, 2023, which is fully incorporated by reference herein), the outer jacket 205 of the shaft 20 extending proximally into the interior of the handle 50 until the outer jacket 205 terminates. The inner channel 206, on the other hand, also extends proximally into the interior of the handle 50. However, rather than terminating shortly after entering the handle 50 (as the outer jacket 205 does), the inner channel 206 extends proximally into the handle 50 until it reaches and is bonded to, e.g., sealed so as to prevent leaking, the bifurcation region 32. FIG. 17 also shows portions of the electrical wire 301 and the steering wires 302a, 302b, 302c, 302d. Although shown cut off in the view of FIG. 17 (merely to avoid cluttering the figure), the electrical wire 301 and the steering wires 302a, 302b, 302c, 302d all extend proximally fully into the handle 50 with the electrical wire 301 extending proximally until it is connected to an electrical or computer controller within the handle 50 (as shown and described more fully in applicant's co-pending U.S. Patent Application Ser. No. 63/499,681 filed May 2, 2023, which is fully incorporated by reference herein), and the steering wires 302a, 302b, 302c, 302d extending proximally until they are connected to respective ones of the roller wheels within the handle 50, as set forth in greater detail above.

There are no limitations in terms of the particular embodiments described in this application, which are intended as illustrations of various aspects only. Many modifications and variations can be made without departing from its spirit and scope, as will be apparent to those skilled in the art. Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An endoscope for use in a surgical procedure, comprising:
    a handle for gripping by a user, the handle including a common shaft to which a rotatable left/right steering roller wheel is keyed and about which a rotatable up/down steering thumb knob is freely rotated; and
    a shaft extending from the handle and configured to be longitudinally inserted into a patient;
    the shaft including an outer jacket defining an outer surface of the shaft,
    the shaft also including an inner channel defining a working channel extending longitudinally through the shaft,
    the shaft including an open space between the outer jacket and the inner channel,
    the shaft also including an electrical wire extending longitudinally within the open space.

2. The endoscope of claim 1, wherein the outer jacket includes braided filaments.

3. The endoscope of claim 1, wherein the outer jacket includes an outer protective layer.

4. The endoscope of claim 1, wherein the outer jacket defines a plurality of longitudinally-extending lumens.

5. The endoscope of claim 4, further comprising:
    a plurality of longitudinally-extending steering wires, each one of the plurality of longitudinally-extending steering wires extending through a respective one of the plurality of longitudinally-extending lumens.

6. The endoscope of claim 5, wherein each one of the plurality of longitudinally-extending lumens is defined by a respective one of a plurality of tubular sheaths.

7. The endoscope of claim 6, wherein the plurality of tubular sheaths are more lubricious than the material from which the outer jacket is formed, such that the steering wires may move more easily therewithin.

8. The endoscope of claim 6, wherein the plurality of tubular sheaths are formed from a material that is more durable than the material from which the outer jacket is formed, such that the movement of the steering wires through the tubular sheaths is less likely to puncture or damage the material of the outer jacket.

9. The endoscope of claim 1, further comprising at least one of an illumination source and an imaging device located at the distal end of the shaft, the illumination source and the imaging device being connected via the electrical wire to an electronic control module in the handle.

10. The endoscope of claim 1, further comprising:
    a control mechanism in the handle actuatable by a user to selectively control the flow of at least one of air, suction or water through the working channel.

11. An endoscope for use in a surgical procedure, comprising:
    a handle for gripping by a user, the handle having opposing roller knobs and a rotatable thumb knob that rotate about a shared axis of rotation; and
    a shaft extending from the handle and configured, upon being longitudinally inserted into a patient, to be steered in left and right directions by the opposing roller knobs and to be steered in up and down directions by the thumb knob;

the shaft including an outer jacket, the outer jacket having an outer surface that defines an outer surface of the shaft, the outer jacket also having an inner surface, the shaft also including an inner channel, the inner channel having an outer surface, the inner channel also having an inner surface defining a working channel extending longitudinally through the shaft, the shaft defining an open space between the inner surface of the outer jacket and the outer surface of the inner channel, the open space between the inner surface of the outer jacket and the outer surface of the inner channel increasing the flexibility of the shaft along its entire length.

12. The endoscope of claim 11, further comprising:
an electrical wire extending longitudinally within the open space.

13. The endoscope of claim 11, wherein the outer jacket includes braided filaments.

14. The endoscope of claim 11, wherein the outer jacket includes an outer protective layer.

15. The endoscope of claim 11, wherein the outer jacket defines a plurality of longitudinally-extending lumens.

16. The endoscope of claim 15, further comprising:
a plurality of longitudinally-extending steering wires, each one of the plurality of longitudinally-extending steering wires extending through a respective one of the plurality of longitudinally-extending lumens.

17. The endoscope of claim 16, wherein each one of the plurality of longitudinally-extending lumens is defined by a respective one of a plurality of tubular sheaths.

18. The endoscope of claim 17, wherein the plurality of tubular sheaths are more lubricious than the material from which the outer jacket is formed, such that the steering wires may move more easily therewithin.

19. The endoscope of claim 17, wherein the plurality of tubular sheaths are formed from a material that is more durable than the material from which the outer jacket is formed, such that the movement of the steering wires through the tubular sheaths is less likely to puncture or damage the material of the outer jacket.

20. The endoscope of claim 12, further comprising at least one of an illumination source and an imaging device located at the distal end of the shaft, the illumination source and the imaging device being connected via the electrical wire to an electronic control module in the handle.

21. An endoscope for use in a surgical procedure, comprising:
a handle for gripping by a user, the handle including first and second roller knobs that are rotated with a rotatable shaft within the handle and a thumb knob that rotates freely around the same rotatable shaft; and a shaft extending from the handle and configured to be longitudinally inserted into a patient, the shaft including an outer jacket defining an outer surface of the shaft, the outer jacket defining a plurality of longitudinally-extending lumens, a plurality of longitudinally-extending steering wires, each one of the plurality of longitudinally-extending steering wires extending through a respective one of the plurality of longitudinally-extending lumens, the plurality of longitudinally-extending steering wires arranged at 0, 90, 180 and 270 degrees around the circumference of the shaft as measured from the topmost region of the shaft, a first pair of the plurality of longitudinally-extending steering wires connected to the respective roller knobs on the handle such that movement by a user of the roller knobs causes corresponding movement of the shaft in 90 and 270 degree directions, and a second pair of the plurality of longitudinally-extending steering wires connected to the thumb knob on the handle such that movement by a user of the thumb knob causes corresponding movement of the shaft in 0 and 180 degree directions.

22. The endoscope of claim 21, wherein the outer jacket also has an inner surface.

23. The endoscope of claim 22, wherein the shaft also including an inner sheath, the inner sheath having an outer surface, the inner sheath also having an inner surface defining a working channel extending longitudinally through the shaft, the shaft including an open space between the inner surface of the outer jacket and the outer surface of the inner channel.

24. The endoscope of claim 23, further comprising:
an electrical wire extending longitudinally within the open space.

25. The endoscope of claim 21, wherein the outer jacket includes braided filaments.

26. The endoscope of claim 21, wherein the outer jacket includes an outer protective layer.

27. The endoscope of claim 21, wherein each one of the plurality of longitudinally-extending lumens is defined by a respective one of a plurality of tubular sheaths.

28. The endoscope of claim 27, wherein the plurality of tubular sheaths are more lubricious than the material from which the outer jacket is formed, such that the steering wires may move more easily therewithin.

29. The endoscope of claim 27, wherein the plurality of tubular sheaths are more durable than the material from which the outer jacket is formed, such that the movement of the steering wires is less likely to puncture or damage the material of the outer jacket.

* * * * *